(12) United States Patent
Milczek et al.

(10) Patent No.: US 12,256,741 B2
(45) Date of Patent: Mar. 25, 2025

(54) PRESERVATIVE COMPOSITIONS AND METHODS OF USE THEREOF

(71) Applicant: Curie Co. Inc., New York, NY (US)

(72) Inventors: Erika Milczek, New York, NY (US); Simone Costa, New York, NY (US); William Shindel, New York, NY (US)

(73) Assignee: Curie Co. Inc., New York, NY (US)

( * ) Notice: Subject to any disclaimer, the term of this patent is extended or adjusted under 35 U.S.C. 154(b) by 756 days.

(21) Appl. No.: 17/436,542

(22) PCT Filed: Mar. 5, 2020

(86) PCT No.: PCT/US2020/021211
§ 371 (c)(1),
(2) Date: Sep. 3, 2021

(87) PCT Pub. No.: WO2020/181099
PCT Pub. Date: Sep. 10, 2020

(65) Prior Publication Data
US 2022/0117236 A1    Apr. 21, 2022

Related U.S. Application Data

(60) Provisional application No. 62/814,582, filed on Mar. 6, 2019.

(51) Int. Cl.
| | | |
|---|---|---|
| A01N 63/50 | (2020.01) | |
| C12N 9/10 | (2006.01) | |
| C12N 11/10 | (2006.01) | |
| C12N 15/52 | (2006.01) | |

(52) U.S. Cl.
CPC .......... *A01N 63/50* (2020.01); *C12N 9/1044* (2013.01); *C12N 11/10* (2013.01); *C12N 15/52* (2013.01); *C12Y 203/02013* (2013.01)

(58) Field of Classification Search
CPC ...... A01N 63/50; C12N 9/1044; C12N 11/10; C12N 15/52; C12Y 203/02013
See application file for complete search history.

(56) References Cited

U.S. PATENT DOCUMENTS

| | | |
|---|---|---|
| 3,284,212 A | 11/1966 | Tribble et al. |
| 6,433,078 B1 | 8/2002 | Gololobov et al. |
| 8,679,526 B2 | 3/2014 | Van Den Plas et al. |
| 2009/0285890 A1 | 11/2009 | Van Den Plas et al. |

FOREIGN PATENT DOCUMENTS

| | | |
|---|---|---|
| CN | 101600835 A | 12/2009 |
| CN | 102762668 A | 10/2012 |
| CN | 104522117 | 4/2015 |
| CN | 108157582 A | 6/2018 |
| EP | 3272864 A1 | 1/2018 |
| JP | H09149784 A | 6/1997 |
| JP | 2001-061423 A | 3/2001 |
| JP | 2014-155463 A | 8/2014 |
| KR | 100550385 | 2/2006 |
| WO | WO 2008/063902 A2 | 5/2008 |
| WO | WO 2011/079187 A1 | 6/2011 |
| WO | WO 2013/071284 A1 | 5/2013 |

OTHER PUBLICATIONS

I. Fernandez-Bats, et al. "Bioactive mesoporous silica nanocomposite films obtained from native and transglutaminase-crosslinked bitter vetch proteins," Food Hydrocolloids 82 (2018) 106-115. (Year: 2018).*
S. Datta, L. R. Christena, Y. Rani, S. Rajaram. "Enzyme immobilization: an overview on techniques and support materials," 3 Biotech 3, 1-9 (2013). (Year: 2013).*
E.I.Rabea, et al. "Chitosan as Antimicrobial Agent: Applications and Mode of Action," Biomacromolecules, vol. 4, No. 6, 2003, 1457-1465. (Year: 2003).*
International Search Report and Written Opinion for International Application No. PCT/US2020/021211, dated Jul. 15, 2020, 15 pages.
Wikipedia entry for "Food Spoilage," https://en.wikipedia.org/w/index.php?title-Food_spoilage&oldid-872653949; last edited Dec. 8, 2018, 2 pages.
Wikipedia entry for "Preservative," https://en.wikipedia.org/w/index.php?title=Preservative&oldid=875919351; Dec. 29, 2018, 4 pages.
Tokay et al., "Shelf-Life Extension of Fish Fillets by Spraying with Microbial Transglutaminase," Journal of Aquatic Food Product Technology, 2017, 26:8, 940-948.
Activa® GS Material Safety Data Sheet, Ajinomoto, Jul. 7, 2014, 2 pages.
Activa® GS Allergen Statement, Ajinomoto, Oct. 17, 2014, 1 page.
Activa® GS Transglutaminase, Modernist Pantry, LLC, https://modernistpantry.com/products/activa-gs-transglutaminase.html, Apr. 5, 2022, 5 pages.
Activa® GS Specifications, Ajinomoto, 1 page.
ACTIVA® Product Information, Ajinomoto, 2 pages.
Lu et al., "Application of Gelatin in Food Packaging: A Review," Polymers, 2022, 14(3): 436, pp. 1-19.

(Continued)

*Primary Examiner* — Michael P Cohen
(74) *Attorney, Agent, or Firm* — Finnegan, Henderson, Farabow, Garrett & Dunner LLP

(57) ABSTRACT

Antimicrobial preservative compositions that can be incorporated in products to be preserved are disclosed herein. The disclosed compositions include immobilized biocidal enzymes, such as cross-linking enzymes or active enzymes falling into the zymogen-class, for the purpose of modifying amino acid residues on a protein or binding a molecule of interest to a protein. The compositions include enzymes that are immobilized on a polymeric solid support, which improve the shelf life of the enzyme and protect the enzyme from auto-cross-linking or other deterioration over extended storage periods. Also disclosed are methods of increasing the self-like of products, such as personal care, household and industrial products, by incorporating an effective amount of the disclosed compositions into the product.

6 Claims, 8 Drawing Sheets

(56) References Cited

OTHER PUBLICATIONS

Abdullah et al., "Immobilization of Tyrosinase in Chitosan Film for an Optical Detection of Phenol," Sensors and Actuators B: Chemical, 2006, 114(2):604-609.
Carvalho et al., "L-DOPA Production by Immobilized Tyrosinase," Applied Biochemistry and Biotechnology, 2000, vol. 84-86:791-800.
Dinçer, et al., "Immobilization of Tyrosinase on Chitosan—Clay Composite Beads," International Journal of Biological Macromolecules, 2012, 50(3):815-820.
Jadán et al., "Selective Determination of Lysine in Dry-Cured Meats Using a Sensor Based on Lysine-α-Oxidase Immobilised on a Nylon Membrane," Food Anal Methods, 2016, 9(9):2484-2490.
Lucas-Elío et al., "The Antimicrobial Activity of Marinocine, Synthesized by *Marinomonas mediterranea*, is Due to Hydrogen Peroxide Generated by Its Lysine Oxidase Activity," Journal of Bacteriology, 2006, 188(7):2493-2501.
Munjal et al., "Stability and Properties of Mushroom Tyrosinase Entrapped in Alginate, Polyacrylamide and Gelatin Gels," Enzyme and Microbial Technology, 2002, 30(5):613-619.

\* cited by examiner

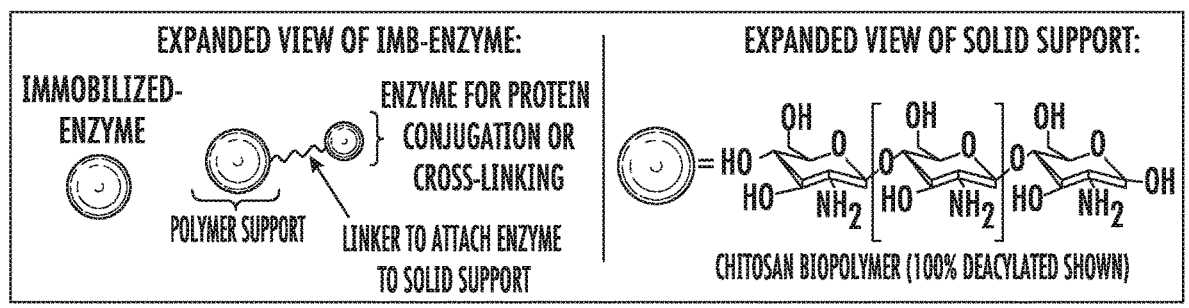
FIG. 1 ANATOMY OF DEVICE: POLYMER, LINKER, ENZYME
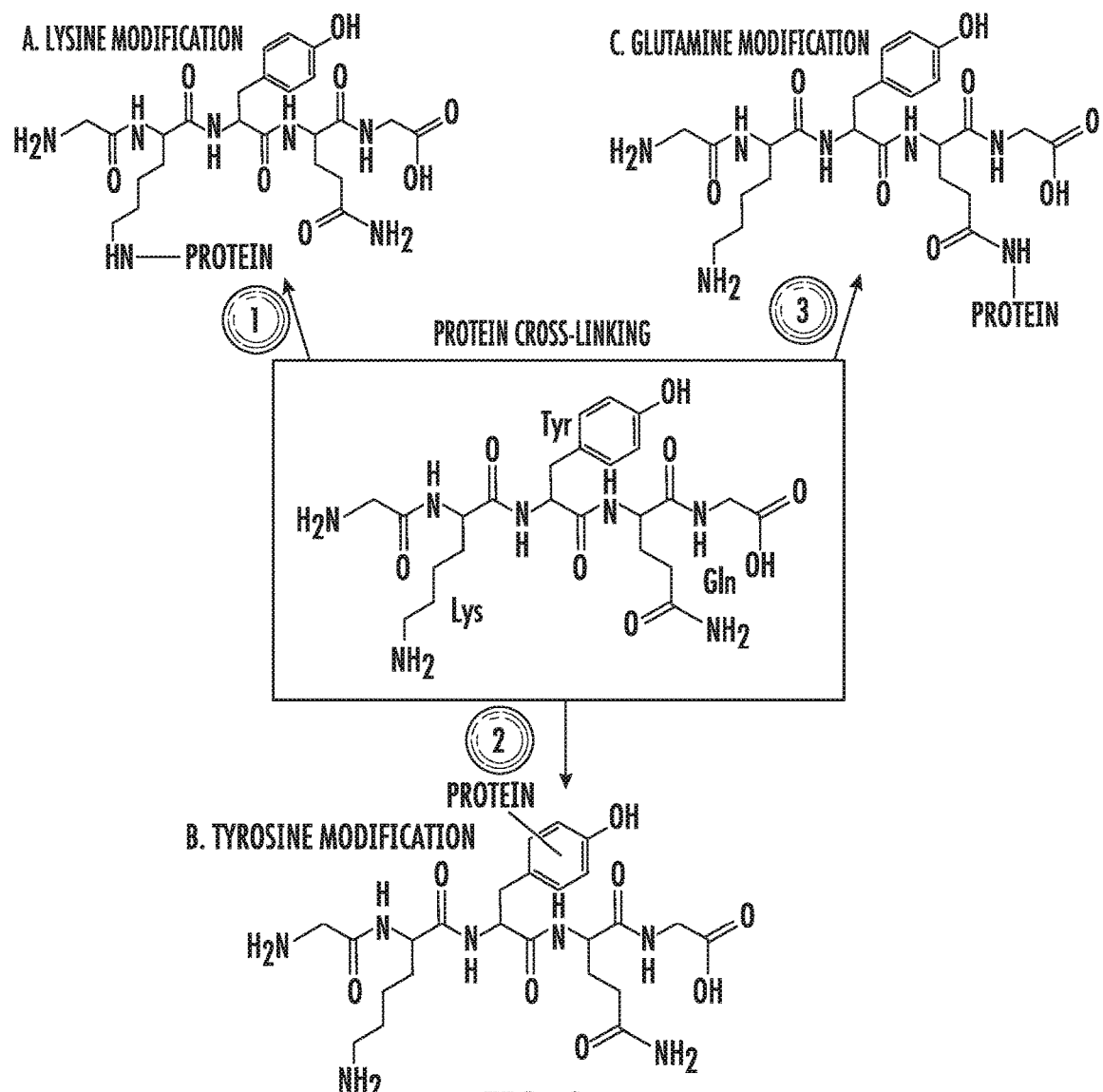
FIG. 2 ENZYME CATALYZED CROSS-LINKNG

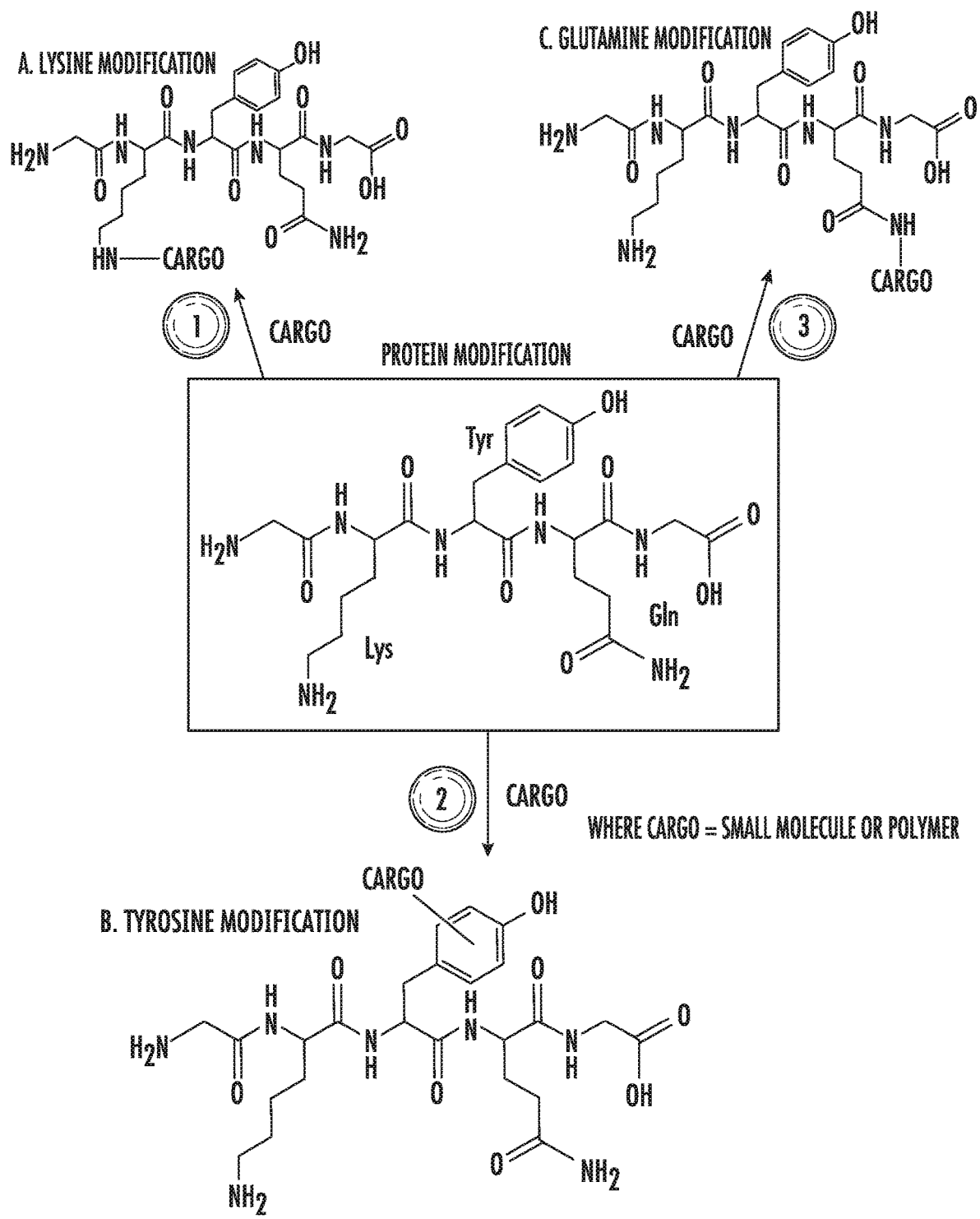
FIG. 3  ENZYME CATALYZED ADDITION OF MOLECULAR CARGO

Fig. 4
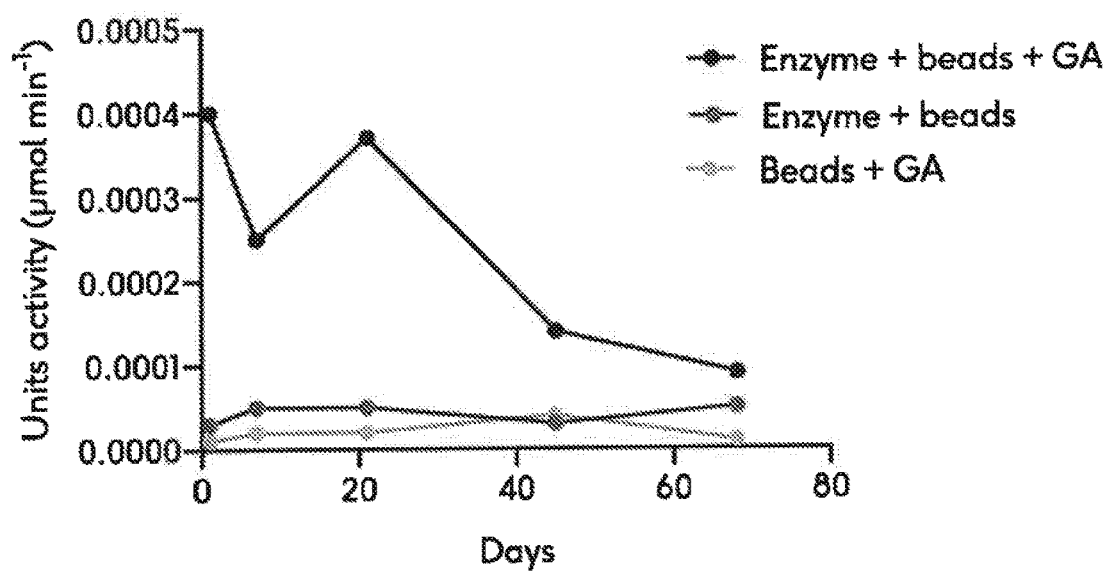
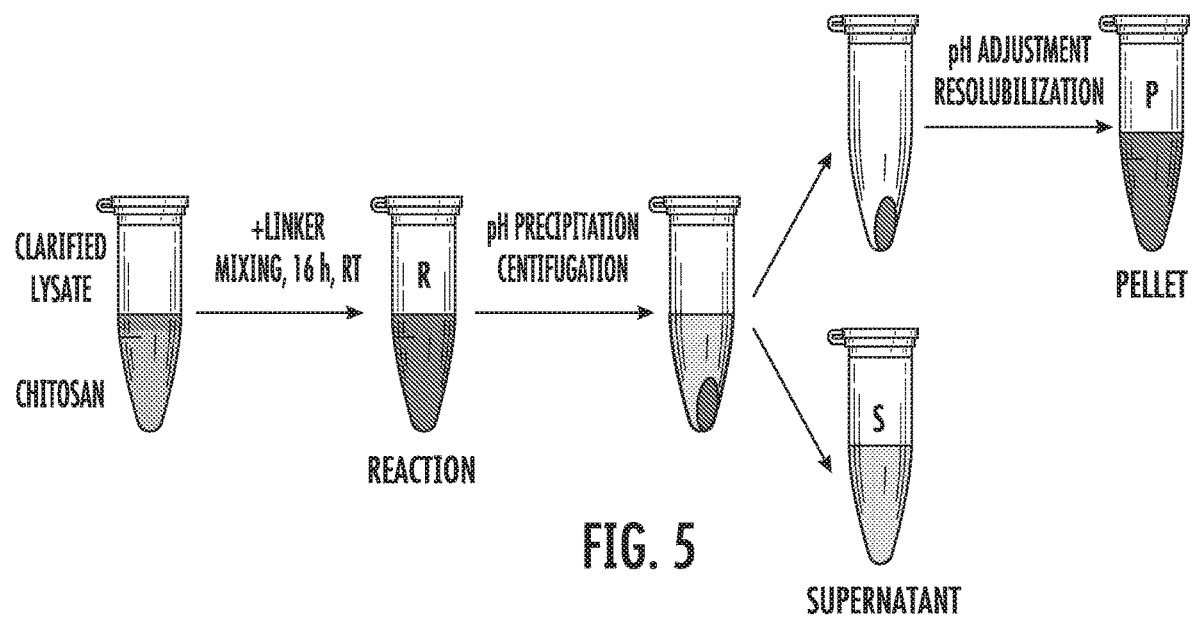
FIG. 5

Fig. 9C
*C. albicans*
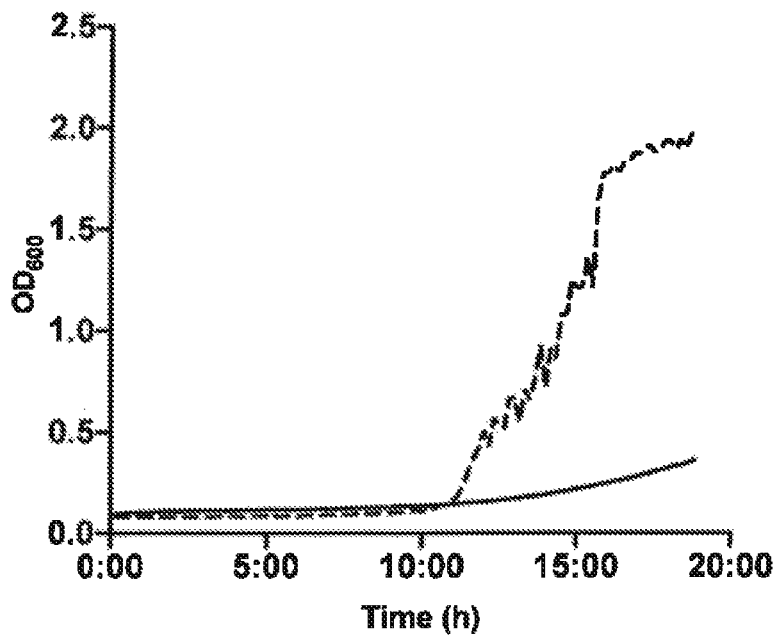
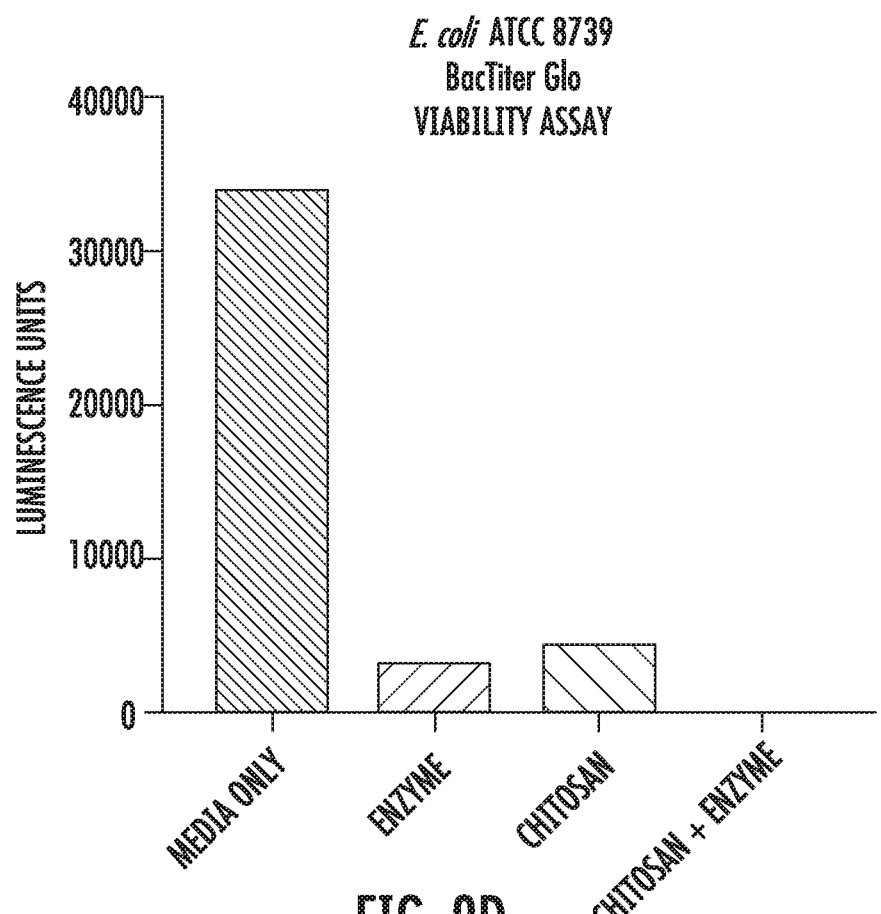
FIG. 9D

PRESERVATIVE COMPOSITIONS AND METHODS OF USE THEREOF

CROSS-REFERENCE TO RELATED APPLICATIONS

This application is a U.S. National Stage Application under 37 C.F.R. $371 of PCT Application No. US2020/021211, filed on Mar. 5, 2020, which claims the benefit of U.S. Provisional Application No. 62/814,582, filed on Mar. 6, 2019, which is incorporated by reference herein in its entirety.

STATEMENT REGARDING FEDERALLY SPONSORED RESEARCH

This invention was partially made with government support under Grant No. 2026057, awarded by the National Science Foundation. The government has certain rights in this invention.

FIELD OF THE INVENTION

The present invention relates to active enzymes derived from zymogen proteins and their use as biocidal (e.g., cross-linking) agents. These biocidal enzymes can be bound to a polymeric support to form an enzymatic device, for increased shelf life of a biocidal enzyme. The enzymatic device can be used to cross-link proteins or to modify proteins of interest, such as binding a molecule, protein, or peptide to another protein. More specifically, the enzyme(s) may be employed as biocidal agents for novel preservatives and as antimicrobials for healthcare products, personal care or cosmetic formulations, food, pharmaceuticals, packaging, and marine applications.

BACKGROUND OF THE INVENTION

Preservative compositions for protecting and preserving formulations against bacterial or fungal attack are known in the art, and have a wide variety of applications in fields such as personal care products, household and industrial products, health and hygiene products, and pharmaceuticals. There are many chemicals, small molecules and preservatives that are used as biocidal agents. Conventional preservative blends have included traditional active ingredients such as formaldehyde releasers and/or parabens, due to the good bacterial and fungicidal properties achieved by these types of compounds.

One of the more common biocidal mechanisms is protein acylation and subsequent protein cross-linking using formaldehyde and glutaraldehyde. Gamma irradiation is another method that catalyzes cellular decomposition through cross-linking activity. Gamma irradiation is frequently employed for sterilization.

In addition to chemicals and small molecules, biocidal enzymes and proteins have been used as biocompatible preservatives in the food (Malhotra, et al., *Frontiers in Microbiology* 2015, 6, 611), healthcare (Kaplan, et al., *Journal of Dental Research* 2010, 89, 205-218), and marine (Olsen, et al. (2007) *Biofouling* 23:369-383) industries. Examples of these enzymes include: oxidases and peroxidases, which generate oxidizing species for biocidal activity; lytic enzymes, like proteases and lyases (e.g., savinase, lysozyme, lysostaphin, subtilisin), which degrade the surface of microbes (e.g., fungi, viruses, bacteria); lactoferrin, which hydrolyzes nucleic acids, such as RNA; and antimicrobial peptides (e.g., nisin, periocin), which are believed to kill microbes by creating pores in the cell wall, resulting in cell rupture and leakage of cell contents.

Known biocidal agents often cause damage to the products that they are deployed to protect from microbial contamination. For example, U.S. Pat. No. 5,326,561 discloses an enzyme fungicide cocktail using chitinolytic enzymes, glucanolytic enzymes and cellulases, which are lytic enzymes. However, lytic enzymes can destroy consumer product formulations that contain esters, which are used as conditioners and shine increasing agents, proteins (e.g., keratin and peptide hair/skin conditions), and/or carbohydrates (e.g., gums and other thickeners). Further, biologic preservatives can deteriorate over time, reducing the shelf life of a product. There is a need for agents with antimicrobial (e.g., bactericidal and fungicidal) activity which avoid these problems.

SUMMARY OF THE INVENTION

It is an object of the present invention to provide preservative compositions that can be incorporated into products to be preserved, as disclosed herein.

It is a further object of the present invention to provide a method of increasing the shelf-life of products, such as personal care, household, industrial, food, pharmaceutical, cosmetic, healthcare, and marine products.

It is a further object of the present invention to provide products, such as personal care, household, industrial, food, pharmaceutical, cosmetic, healthcare, and marine products, with improved shelf life.

It is a further object of the present invention to provide a method of removing an enzyme from an industrial process or reaction mixture, by precipitation of the industrial enzyme in a polymer-bound form, via a shift in pH for a reaction catalyzed by the enzyme, leaving a protein or peptide of interest that is modified by the industrial enzyme in solution. This aids in facile recovery and purification of the protein, or peptide, of interest from the reactive enzyme.

It is a further object of the present invention to provide a method of preparing antimicrobial performance devices, such as those found in wound care and bandages, by incorporation of a cross-linking enzyme.

Preservative compositions that can be incorporated into products to be preserved are disclosed herein. The disclosed compositions include immobilized or conjugated enzymes, such as enzymes which are initially secreted as zymogens, on a polymer support structure. Examples of zymogen classes of enzymes include, but are not limited to, hydrolases, proteases, lytic enzymes, and cross-linking enzymes. In one embodiment, the compositions include a cross-linking enzyme, or another zymogen class of enzyme, immobilized or conjugated (e.g., covalently bound) to a polymer support, which may improve the shelf life, e.g., preserve catalytic activity, of the enzyme over a commercially relevant time frame, and/or protect the enzyme from auto-cross-linking and/or deterioration (e.g., decrease in catalytic activity) over extended storage periods. In one embodiment, the enzyme is a cross-linking enzyme or an enzyme from another class of zymogen enzymes. For example, the enzyme, may react amino acid residues on a protein through cross-linking or binding a molecule of interest to a protein (e.g., conjugation of a small molecule, protein, or peptide to another protein). In one embodiment, a cross-linking enzyme or other zymogen class enzyme is covalently bound to a polymeric support, e.g., chitosan, via a linker. In another embodiment a cross-linking enzyme or other zymogen class enzyme is immobilized on, e.g., covalently bound directly to, the polymeric support without use of a linker. In some embodiments, the polymer is a biopolymer. In some embodiments, the polymer is a biocidal polymer, such as, but not limited to, chitosan or carboxymethylchitosan. In some embodiments, the compositions include one or more enzyme, such as a cross-linking enzyme, hydrolase, protease, and/or lytic enzyme, immobilized on a polymeric support as disclosed herein, in an effective amount to inhibit (reduce or eliminate) microbial (e.g., bacterial) growth in a product to be preserved.

Also disclosed is a method of increasing the shelf-like of products, such as personal care, household, industrial, food, pharmaceutical, cosmetic, healthcare, and marine products, including incorporating an effective amount of a composition as disclosed herein into the product or a formulation or composition that includes the product. In some embodiments, the product does not include any other preservative substance or composition in addition to the enzyme/polymer composition disclosed herein. In some embodiments, the product includes at least one other preservative substance or composition in addition to the enzyme/polymer composition disclosed herein. In some embodiments, the product does not include formaldehyde or glutaraldehyde as a preservative. In some embodiments, the product includes at least one other preservative substance or composition, in addition to the enzyme/polymer composition disclosed herein, that is not formaldehyde or glutaraldehyde In some embodiments, the shelf life of the product incorporating the composition is increased when compared to the same product not incorporating the composition.

Also disclosed are products such as personal care, household, industrial food, pharmaceutical, cosmetic, healthcare, marine, painting, coating, or energy products, or formulations or compositions that include the product, which include an effective amount of a composition as disclosed herein and have improved shelf life when compared the shelf life of a product which does not include an additional added preservative or when compared to the same product that does not include the composition.

In some embodiments, a polymer immobilized or conjugated enzyme as disclosed herein may bind a molecule of interest to a protein. Nonlimiting examples include: binding of a dye molecule to a protein, such as collagen, keratin, or elastin; binding of a protein or peptide to another protein, such as collagen, keratin, or elastin; and binding of a pharmaceutical (drug) molecule to a protein, for example, formation of an antibody-drug conjugate.

In one aspect, preservative compositions are provided that include one or more zymogen-class enzyme immobilized on or encapsulated within a polymeric support structure. For example, the enzyme may be selected from a hydrolase, a protease, a lytic enzyme, and a cross-linking enzyme, or combinations thereof. In one embodiment, the enzyme is a cross-linking enzyme, such as a transglutaminase, a laccase, a peroxidase, a transferase, a lysyl oxidase, or a tyrosinase. In some embodiments, the polymeric support structure includes a biocidal polymer. In an embodiment, the polymer is reversibly soluble. The enzyme may be covalently bound to the polymer, such as via a linker. In some embodiments, the polymer is in the form of beads, such as microbeads. In an embodiment, the polymer is in the form of biodegradable polymeric beads, such as biodegradable microbeads. In some embodiments, the enzyme is encapsulated in the polymer. In some embodiments, the polymer is selected from chitin, chitosan, carboxymethylchitosan, polylysine, cellulose, quaternary ammonium cellulose, alginate, pectin, and carboxycellulose, or combinations thereof.

In another aspect, methods are provided for increasing the shelf-like of a product, which include incorporating a zymogen-class enzyme into a product in an amount effective to prevent or decrease growth of one or more microbe, in comparison to an identical product that does not include the enzyme. For example, the enzyme may be selected from a hydrolase, a protease, a lytic enzyme, and a cross-linking enzyme, or combinations thereof. In one embodiment, the enzyme is a cross-linking enzyme, such as a transglutaminase, a laccase, a peroxidase, a transferase, a lysyl oxidase, or a tyrosinase.

In another aspect, methods are provided for increasing the shelf-like of a product, which include incorporating a preservative composition that includes one or more zymogen-class enzyme immobilized on or encapsulated within a polymeric support structure, as described herein, into the product in an amount effective to prevent or decrease growth of one or more microbe in comparison to an identical product that does not comprise the composition. For example, the enzyme may be selected from a hydrolase, a protease, a lytic enzyme, and a cross-linking enzyme, or combinations thereof. In one embodiment, the enzyme is a cross-linking enzyme, such as a transglutaminase, a laccase, a peroxidase, a transferase, a lysyl oxidase, or a tyrosinase. In some embodiments, the polymeric support structure includes a biocidal polymer. In an embodiment, the polymer is reversibly soluble. The enzyme may be covalently bound to the polymer, such as via a linker. In some embodiments, the polymer is in the form of beads, such as microbeads. In an embodiment, the polymer is in the form of biodegradable polymeric beads, such as biodegradable microbeads. In some embodiments, the enzyme is encapsulated in the polymer. In some embodiments, the polymer is selected from chitin, chitosan, carboxymethylchitosan, polylysine, cellulose, quaternary ammonium cellulose, alginate, pectin, and carboxycellulose, or combinations thereof.

In another aspect, products are provided that include a zymogen-class enzyme in an effective amount to increase the shelf life of the product, in comparison to an identical product that does not comprise the enzyme. For example, the enzyme is included in an amount that is effective to prevent or decrease growth of one or more microbe, in comparison to an identical product that does not comprise the composition.

In some embodiments, the enzyme is selected from a hydrolase, a protease, a lytic enzyme, and a cross-linking enzyme, or combinations thereof. In one embodiment, the enzyme is a cross-linking enzyme, such as a transglutaminase, a laccase, a peroxidase, a transferase, a lysyl oxidase, or a tyrosinase.

In some embodiments, the polymeric support structure includes a biocidal polymer. In an embodiment, the polymer is reversibly soluble. The enzyme may be covalently bound to the polymer, such as via a linker. In some embodiments, the polymer is in the form of beads, such as microbeads. In an embodiment, the polymer is in the form of biodegradable polymeric beads, such as biodegradable microbeads. In some embodiments, the enzyme is encapsulated in the polymer. In some embodiments, the polymer is selected from chitin, chitosan, carboxymethylchitosan, polylysine, cellulose, quaternary ammonium cellulose, alginate, pectin, and carboxycellulose, or combinations thereof.

In some embodiments, the product is a personal care, household, industrial, food, pharmaceutical, cosmetic, healthcare, marine, paint, coating, energy, plastic, packaging, or agricultural product. For example, the product may be a personal care product selected from bar soap, liquid soap, hand sanitizer, preoperative skin disinfectant, cleansing wipes, disinfecting wipes, body wash, acne treatment products, antifungal diaper rash cream, antifungal skin cream, shampoo, conditioner, cosmetics deodorant, antimicrobial creams, body lotion, hand cream, topical cream, aftershave lotion, skin toner, mouth wash, toothpaste, and sunscreen lotion. For example, the product may be a wound care product selected from wound healing ointments, creams, and lotions, wound coverings, burn wound cream, bandages, tape, and steri-strips.

In some embodiments, at least about 90% of enzyme activity is retained over a period of 28 days. In some embodiments, the enzyme activity is retained at pH of about 4 to about 9 and temperature of about 4° C. to about 40° C. In some embodiments, microbial growth is inhibited by at least about 80% over a period of 28 days at about pH 4 to about pH 9, and temperature of about 4° C. to about 40° C.

In some embodiments, the product does not include any other preservative substance. In other embodiments, the product includes at least one other preservative substance, such as, but not limited to, at least one petrochemical derived preservative substance.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 shows a cross-linking (or acylating) enzyme bound to a polymer support. The polymer support shown is chitosan (the fully deacetylated form).

FIG. 2 shows the use of the immobilized enzymes for cross-linking proteins via lysine, tyrosine, and glutamine amino acid residues.

FIG. 3 shows the use of the immobilized enzymes for modifying proteins with cargo (e.g., covalently attaching cargo, such as small molecules or polymers) via lysine, tyrosine, and glutamine amino acid residues.

FIG. 4 shows stability of transglutaminase-polymer bead conjugates as described in Example 3.

FIG. 5 shows a method for encapsulating enzyme with free monomers as described in Example 4.

FIG. 9C shows Growth inhibition of *C. albicans* in the presence of 880 mg $L^{-1}$ (or 0.088% w/v) Curie Co mTG (solid black line). Dashed grey line shows growth in media only.

FIG. 9D shows final cell viability of *E. coli* ATCC 8739 cultures after 16 h growth as measured by the BacTiter Glow cell viability assay (Promega). Luminescent signal is an indicator of population viability as it is proportional to the amount of ATP produced by viable cells. Enzyme is 440 mg $L^{-1}$ (or 0.044% w/v) Curie Co mTG. Chitosan is 0.025% w/v. Chitosan+enzyme is the combination of the two at the same concentrations.

DETAILED DESCRIPTION OF THE INVENTION

Figure 6A:
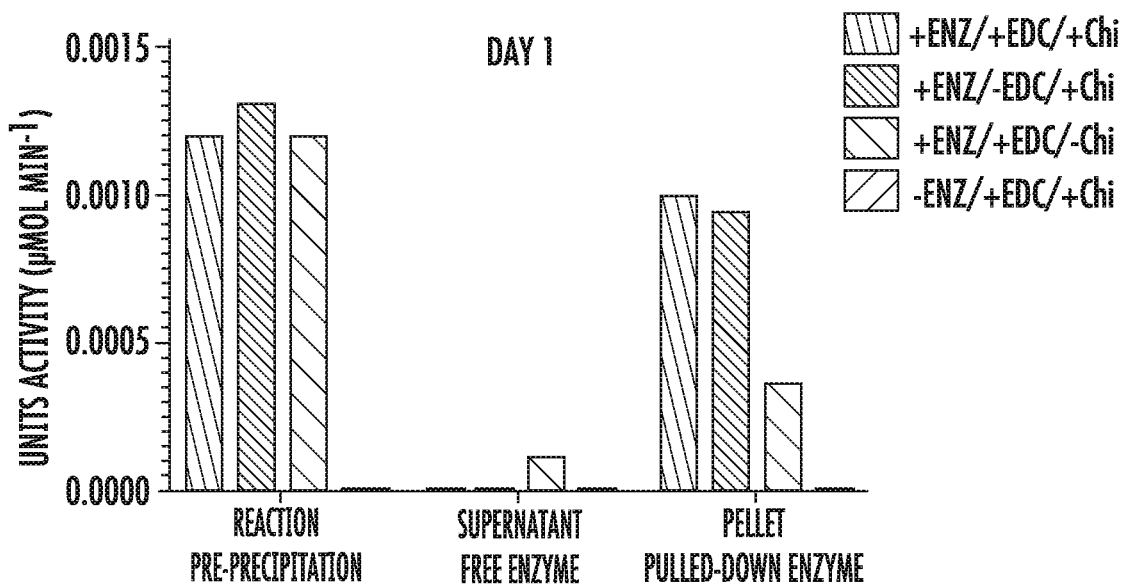
FIGS. 6A-6B show stability of carboxymethylchitosan encapsulated transglutaminase as described in Example 5.

Biocidal enzymes, biocidal enzyme-polymer conjugates, and polymer encapsulated biocidal enzymes are described herein. Enzyme-polymer conjugates and encapsulated enzymes demonstrate superior stability relative to unconjugated or unencapsulated enzymes over several months at pH 4.5, which is a relevant pH range for cosmetic skincare applications. A biocidal enzyme and mutant form of the enzyme have been found to exhibit antimicrobial properties. When mixing the enzyme with known antimicrobial polymers the antimicrobial activity of both the enzyme and polymer have potentiated effect on antimicrobial activity. The polymer enhances the stability of the enzyme, allowing for longer shelf life of the enzyme, and mutant forms of the enzyme, and consequently a product into which the enzyme is incorporated, under a broad range of pH conditions.

I. Definitions

"A," "an" and "the" include plural references unless the context clearly dictates, thus the indefinite articles "a", "an,", and "the" as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein, the term "composition" refers to a combination of two or more substances, including an immobilized enzyme (e.g., preservative) composition as described herein.

As used herein, the term "product" is intended to refer to a preparation, composition, or article of manufacture that has a specific utility that is to be preserved with an immobilized enzyme composition as described herein.

As used herein, "preservative" is an agent added to a product as described to prevent (for some period of time) the growth of microorganisms, or the occurrence of undesirable chemical reactions (such as oxidation), that spoil or deteriorate, including deterioration of one or more utility, of the product.

"Encapsulate" or "encapsulation" as used herein refers to the entrapment or enclosure of an enzyme in a matrix. The matrix can be polymer alone or polymer with a cross-linking agent to covalently bind the enzyme to the polymer or to a porous polymeric network structure of the matrix or to a semi-permeable membrane coating containing the enzyme.

The term "conjugate" refers to a covalent, ionic, or electrostatic bond, such as a bond between an enzyme and a polymer.

A "reversibly soluble polymer" refers to a polymer which can phase transition from a soluble to insoluble material in solution in response to controllable stimuli in the environment, such as, but not limited to, pH or ionic strength. This transition process can be repeatably cycled between phases.

"Effective amount" as used herein refers to an amount (e.g., minimum inhibitory concentration (MIC)) of a preservative composition as disclosed herein that is sufficient to prevent or inhibit microbial growth. The preservative compositions of this patent are active against Gram positive bacteria, Gram negative bacteria, yeast, and/or mold.

"Shelf life" refers to the length of time for which an item (e.g., a product as described herein) remains usable, fit for consumption, or saleable.

"Household products" are products, other than personal care products, that would be used by individual consumers.

"Industrial products" refers to products that are used in industry.

"Emollients" are externally applied agents that soften or soothe skin, and are generally known in the art and listed in compendia, such as the "Handbook of Pharmaceutical Excipients", 4$^{th}$ Ed., Pharmaceutical Press, 2003.

"Emulsifiers" are surface active substances which promote the suspension of one liquid in another and promote the formation of a stable mixture, or emulsion, of hydrophobic and hydrophilic substances, such as oil and water.

"Surfactants" are surface-active agents that lower surface tension and thereby increase the emulsifying, foaming, dispersing, spreading, and/or wetting properties of a composition or product.

A "bead" refers to a solid particle, comprising or consisting of a polymer as described herein.

A "microbead" refers to a bead that is less than one millimeter in its largest dimension.

"Biodegradable" refers to a substance that is capable of decomposition by microbes (e.g., bacteria) or other living organisms.

The term "amino acid" refers to a molecule containing both an amine group and a carboxyl group that are bound to a carbon, which is designated the alpha-carbon. Suitable amino acids include, without limitation, both the D- and L-isomers of the naturally occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

The term "catalyst" refers to a chemical actor, such as a molecule or macromolecular structure, which accelerates the speed at which a chemical reaction occurs where a reactant or reactants is converted into a product or products, while the catalyst is not turned into a product itself, or otherwise changed or consumed at the completion of the chemical reaction. After a catalyst participates in one chemical reaction, because it is unchanged, it may participate in further chemical reactions, acting on additional reactants to create additional products. To accelerate a chemical reaction a catalyst decreases the activation energy barrier across the reaction path allowing it to occur at a colder temperature, or faster at a given temperature. In this way, a more rapid approach of the system to chemical equilibrium may be achieved. Catalysts subsume enzymes, which are protein catalysts.

The term "lysate" refers to the liquid containing a mixture and/or a solution of cell contents that result from cell lysis. In some embodiments, the methods described herein comprise a purification of chemicals or mixture of chemicals in a cellular lysate. In some embodiments, the methods comprise a purification of amino acids and/or protein in a cellular lysate.

The term "lysis" refers to the rupture of the plasma membrane and if present, the cell wall of a cell such that a significant amount of intracellular material escapes to the extracellular space. Lysis can be performed using electrochemical, mechanical, osmotic, thermal, or viral means. In some embodiments, the methods described herein comprise performing a lysis of cells or microorganisms as described herein in order to separate a chemical or mixture of chemicals from the contents of a bioreactor. In some embodiments, the methods comprise performing a lysis of cells or microorganisms described herein in order to separate an amino acid or mixture of amino acids and/or proteins from the contents of a bioreactor or cellular growth medium.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

The terms "microorganism" and "microbe" mean microscopic single celled life forms.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also, included within the definition are, for example, polypeptides containing one or more analogs of an amino acid (including, for example, unnatural amino acids, etc.), as well as other modifications known in the art.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e., a single number) can be selected as the quantity, value, or feature to which the range refers. The foregoing applies regardless of whether in particular cases some or all of these embodiments are explicitly disclosed.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated.

II. Compositions

Disclosed are compositions, e.g., preservative compositions, that can be included in or with (e.g., within or associated with) products to be preserved. The disclosed compositions include immobilized enzymes, e.g., cross-linking enzymes (see, e.g., FIG. 1). The immobilized enzyme may catalyze a reaction of amino acid residues on a protein, thereby effecting, for example, protein cross-linking or binding a molecule of interest to a protein (see, e.g., FIGS. 2 and 3). In some embodiments, the compositions include one or more enzyme, e.g., comprising or consisting of one or more cross-linking enzyme, in an amount effective to inhibit microbial (e.g., bacterial) growth, e.g., inhibition of 80% to 100%, or any of at least about 80%, 85%, 90%, 95%, 98%, or 99% of microbial growth, in a product to be preserved. In some embodiments, the enzyme (s) are immobilized on a support that comprises or consists of one or more polymer, optionally a biocidal polymer and/or biopolymer, optionally via a linker, as described herein. In some embodiments, the enzyme(s) are encapsulated in a polymer, e.g., a biocidal polymer and/or biopolymer, as described herein. In some embodiments, the polymer comprises or consists of chitosan or carboxymethylchitosan. In some embodiments, the polymeric support is in the form of a bead, e.g., a biodegradable bead, e.g., a microbead. In some embodiments, the bead, e.g., biodegradable bead, e.g., microbead, comprises or consists of chitosan or carboxymethylchitosan.

Preservatives are antimicrobial ingredients added to product formulations to maintain the microbiological safety of the products by inhibiting the growth of and reducing the amount of microbial contaminants. US Pharmacopeia has published protocols for acceptable microbial survival for preservatives in cosmetics and personal care products. These tests include USP 51 (Antimicrobial Effectiveness Test) and USP 61 (Microbial Limits Test) (https://www.fda.gov/files/about%20fda/published/Pharmaceutical-Microbiology-Manual.pdf).

The effectiveness of the preservative system disclosed herein is determined based on the MIC (minimum inhibitory concentration) against a variety of microbes (e.g. *E. coli* DH10B, *E. coli* ATCC 8739, *B. subtilis* BGSC 1A976, *C. albicans* ATCC 10231, and/or *A. brasiliensis* ATCC 16404). Minimum inhibitory concentrations (MICs) are defined as the lowest concentration of an antimicrobial that will inhibit the growth of a microorganism. Microbial growth may be determined, for example, by spectrophotometric methods (the optical density at 600 nm) or with a cell viability assay (BacTiter Glo, Promega).

In one embodiment, the compositions include an active enzyme, such as a zymogen-class enzyme, for example, but not limited to, a cross-linking enzyme, immobilized on, e.g., covalently bound to or encapsulated in, a polymer support, such as a biocidal polymer, such as, but not limited to, chitosan or carboxymethylchitosan, which may improve the shelf life of the enzyme, and/or protect the enzyme from auto-cross-linking and/or deterioration over extended storage periods. Optionally, the enzyme may be covalently bound to the support via a linker. In one embodiment, a zymogen class enzyme, such as a cross-linking enzyme, is covalently bound to a polymer support, e.g., a biopolymer, such as chitosan or carboxymethylchitosan, via a linker. In another embodiment, a zymogen class enzyme, such as a cross-linking enzyme, is covalently bound to a polymer support, e.g., a biopolymer, such as chitosan or carboxymethylchitosan, without use of a linker.

In one embodiment, the enzyme is a transglutaminase (e.g., *Streptomyces mobaraensis* transglutaminase mutant S2P (e.g., as described in Javitt, et al. (2017) *BMC Biotechnol.* 17:23)), immobilized on or encapsulated in chitosan or carboxymethylchitosan.

A. Enzymes

In some embodiments, a biocidal enzyme utilized in a composition described herein is an enzyme that is initially secreted as a zymogen. Zymogens are inactive enzyme precursors (proenzymes) that are expressed with a pro-sequence that must be cleaved to afford active enzyme. Cleavage of a pro-sequence affords active enzyme that is often highly toxic to cells. A proenzyme is expressed with a cleavable leader sequence to suppress activity of the enzyme, due to related enzyme toxicity to the cell. Therefore, zymogens present a useful class of enzymes for use as antimicrobial agents. The mature active enzyme form (i.e., without the pro-sequence) is used in the disclosed compositions immobilized on a polymeric support, such as chitosan or carboxymethylchitosan, for preparation of a biocidal preservative composition. Useful enzymes within this category include, but are not limited to, hydrolases, proteases, nucleic acid lytic-enzymes, and cross-linking enzymes.

Examples of cross-linking enzymes include, but are not limited to: transglutaminases, laccases, peroxidases, transferases, lysyl oxidases, and tyrosinases. These enzymes have been used to covalently bind small organic molecules, peptides, proteins, cells, and other molecules of interest to polymer or other biopolymer (such as protein or saccharide) scaffolds.

Preferred cross-linking enzymes include transglutaminases, lysyl oxidases, and tyrosinases, which exhibit for cellular toxicity in the active enzyme forms. Due to their auto-cross-linking activity, these cross-linking enzymes are bound to polymer supports, such as chitosan or carboxymethylchitosan, to prevent self-destruction and improve shelf-life. In some embodiments, the polymer possesses biocidal activity. Chitosan and carboxymethyl chitosan have known antimicrobial (biocidal) properties. In some embodiment, a chitosan-enzyme composition (e.g., biocidal enzyme immobilized on chitosan) or a biocidal enzyme immobilized on any of the biocidal polymers disclosed herein has enhanced antimicrobial action, in comparison to the biocidal action of the enzyme or the polymer alone. The biocidal enzyme may be any of the enzymes disclosed herein, such as a zymogen class enzyme, for example, a cross-linking enzyme.

Without being bound by theory, the use of a cross-linking enzyme enhances the antimicrobial properties of chitosan or other biocidal support by providing an additional mechanism of antimicrobial action. Chitosan for example, ruptures the cell membrane and leads to spillage of the cell contents. The cross-linking enzyme can cross-link proteins vital for cell function both on the surface of the cell and within the cell. This combination of both materials together reduce the quantity of the materials needed and provide additional stability to the enzyme allowing for greater activity over time (less chitosan and less enzyme) and reduce the undesirable effects that may accompany the use of biocidal chitosan. Using higher weight percent chitosan in formulations results in acidic product formulations because only protonated chitosan has antimicrobial properties. In other words, higher weight compositions of chitosan correlates with the addition of multiple protonated amines (on the chitosan backbone) into the product in which chitosan is added, for example, personal care products. Highly acidic product formulations may not be desirable for sensory feel or compatible with existing product formulation. Additionally, higher weight percent of chitosan in a formulation leads to increases in viscosity, which also may be undesirable for product formulation. The addition of a second biocidal agent, e.g., a cross-linking enzyme, will allow the amount of chitosan to be reduced while still maintaining biocidal properties. The enzyme alone may be sufficient for preservative/antimicrobial properties, however, immobilization of the enzyme on or encapsulation in a polymeric support, such as chitosan or carboxymethylchitosan, increases the enzymes shelf-life allowing the product formulator to use less enzyme to achieve desirable preservative properties.

(i) Transglutaminase

A transglutaminase (Tgase) is an enzyme that catalyzes the formation of an isopeptide bond between a free amine group of a protein, for example, and the acyl group at the end of the side chain of protein- or peptide-bound glutamine. Such enzymes are classified as EC 2.3.2.13. Transglutaminases catalyze a transamidation reaction between glutamyl and lysyl side chains of target proteins. The catalytic reaction proceeds via glutamine deamination and formation of a protein-glutamyl-thioester at the active site of the enzyme. Nucleophilic attack by a lysyl ε-amino group of a second protein at the carbonyl moiety of the thioester intermediate generates isopeptide-crosslinked proteins that are largely resistant to proteolysis by common peptidases (Mariniello, et al. (2007) J. Agr Food Chem. 55:4717-4721. Bonds formed by a Tgase exhibit high resistance to proteolytic degradation (proteolysis). Proteins possessing Tgase activity have been found in microorganisms, plants, invertebrates, amphibians, fish and birds. Eight mammalian Tgases have been characterized. Examples of Tgases characterized at the protein level are reviewed in Griffin, et al. (2002) Biochem J. 368:377-396. In contrast to eukaryotic Tgases, Tgases from microbial origin are calcium-independent, which represents a major advantage for their practical use.

In some embodiments, the transglutaminase is a microbial transglutaminase, for example $Ca^{2+}$-independent microbial transglutaminase (MTGase) of a variant of Streptomyces mobaraensis. In some particularly preferred embodiments, the Tgase is a microbial Tgase and preferably is the $Ca^{2+}$-independent microbial transglutaminase (MTGase) of a variant of Streptomyces mobaraensis. In some particularly preferred embodiments, the Tgase is a more stable mutational variant of Streptomyces mobaraensis Tgase, such as S2P-Tgase (Javitt, et al. (2017) BMC Biotechnol. 17:23). Well defined prokaryotic Tgases are shown in Table 1, reproduced from Zhang, et al. (2010) Biotechnol. Genet. Eng. Rev. 26:205-222, with additions from Steffen, et al. (2017) J. Biol. Chem. 292(38):15622-15635.

TABLE 1

Well Defined Prokaryotic Tgases

| Year | Strain | Focus of the development | Yield (unit/ml)[a] |
|------|--------|--------------------------|--------------------|
| 1989 | Streptoverticillium mobaraense | Strain isolation | ~2.0 |
| 1996 | Streptoverticillium mobaraense | Substrate optimization | ~1.0 |
| 1997 | Streptoverticillium cinnamoneum | Substrate optimization | ~0.3 |
| 1998 | Streptoverticillium mobaraense | Metabolic optimization | ~1.8 |
| 2000 | Actinomadura sp. | Strain isolation | n/a |
| 2001 | Streptoverticillium mobaraense | Environmental control strategies | 3.37 |
| 2002 | Streptoverticillium mobaraense | Environmental control strategies | 2.94 |
| 2002 | Streptoverticillium mobaraense | Environmental control strategies | 3.40 |
| 2004 | Streptoverticillium ladakanum | Strain isolation | 0.348 |
| 2004 | Streptoverticisllium mobaraense | Substrate optimization | 0.725 |
| 2005 | Streptoverticillium mobaraense | Environmental control strategies | 3.32 |
| 2006 | Bacillus circulans | Strain isolation and substrate optimization | 0.306 |
| 2007 | Streptomyces sp. | Strain isolation and substrate optimization | 1.4 |
| 2007 | Streptomyces hygroscopicus | Strain isolation and environmental control strategies | 5.04 |
| 2008 | Several Streptomyces | Solid fermentation | n/a |
| 2009 | Streptomyces hygroscopicus | Fermentation strategies | 5.79 |
| 2017 | Kutzneria albida | Substrate optimization | n/a |

[a]n/a = not applicable

A Generally Recognized as Safe (GRAS) status has been assigned to transglutaminase preparations from *S. mobaraensis* for protein cross-linking in seafood, meat, dairy, and cereal products (FDA/CFSAN agency response letters: GRAS notice numbers 000004 (1998), 000029 (1999), 000055 (2001), and 000095 (2002)). Commercially available microbial transglutaminase is produced on large scale and distributed under the trade name ACTIVA® by Ajinomoto US, Inc.

(ii) Lysyl Oxidase

Lysyl oxidases (LOX) (also known as protein-lysine 6-oxidase) are copper-dependent enzymes that oxidize primary amine substrates to reactive aldehydes. Five different LOX enzymes have been identified in mammals, LOX and LOX-like (LOXL) 1 to 4, showing a highly conserved catalytic carboxy terminal domain and more divergence in the rest of the sequence. Additionally, LOX proteins have been identified not only in animals, but also in many other eukaryotes, as well as in bacteria and archaea, reviewed in Grau-Bove, et al. (2015) Scientific Reports 5: Article number: 10568.

(iii) Tyrosinase

Tyrosinase (EC 1.14.18.1), usually known as the enzyme responsible for the enzymatic browning of fruits and vegetables, has been demonstrated to induce cross-linking of the whey proteins α-lactalbumin and β-lactoglobulin. Tyrosinases have been isolated and studied from a wide variety of plant, animal, and fungal species.

The best known and characterized tyrosinases are of mammalian origin. The most extensively investigated fungal tyrosinases, both from a structural and functional point of view, are from *Agaricus bisporus* (Withers et al., 1996) and *Neurospora crassa* (Lerch, 1983). Also a few bacterial tyrosinases have been reported, of which *Streptomyces* tyrosinases are the most thoroughly characterized (U.S. Pat. Nos. 5,801,047 and 5,814,495). In addition, tyrosinases have been disclosed, e.g., from *Bacillus* and *Myrothecium* (EP 919 628), *Mucor* (JP 61115488), *Miriococcum* (JP 60062980) *Aspergillus, Chaetomastia*, and *Ascvaginospora* (Abdel-Raheem and Shearer, 2002), and *Trametes* (Tomsovsky and Homolka, 2004).

(iv) Laccase

Laccases are multi-copper oxidases found in plants, fungi, and bacteria, which oxidize phenolic substrates, performing one-electron oxidations, resulting in crosslinking. Methods for cross-linking proteins by laccases have been disclosed, e.g., in US2002/009770. Plant proteins derived from beans, cereals, and animal proteins, including milk, egg, meat, blood, and tendon are listed as suitable substrates. Fungal laccases are disclosed in US2002/019038.

B. Polymeric Support

The compositions described herein include a polymeric support. A biocidal enzyme, as described herein is immobilized on the support, with or without a linker, or encapsulated within a polymeric support, such as a reversibly soluble polymer, including, but not limited to, chitosan, carboxymethylchitosan, or polylysine. In some embodiments, the polymer is a biocidal polymer. Nonlimiting examples of polymeric supports include: chitin, chitosan, carboxymethylchitosan, oxidized cellulose, quaternary ammonium cellulose, alginates, pectin, and carboxycellulose. Preferred supports are biocidal polymers, nonlimiting examples of which are shown in Table 2.

TABLE 2

Examples of Biocidal Polymers for Antimicrobial Applications

| Polymer | Target | Remark |
| --- | --- | --- |
| Quaternary ammonium polyethyleneimine | Gram-positive and Gram-negative bacteria | n-alkylated polyethyleneimine has effective antimicrobial activity, dependent on the hydrophobic and positively charged immobilized long polymeric chains |
| Quaternary phosphonium modified epoxidized natural rubber | *Staphylococcus aureus*, *Escherichia coli* | Moderate growth inhibition of microbes |
| Arginine-tryptophan-rich peptide | Gram-positive and Gram-negative bacteria | Retain antimicrobial functionality for at least 21 days, showing negligible cytotoxicity |
| Guanylated polymethacrylate | *Staphylococcus epidermidis*, *Candida albicans* | Guanidine copolymers were much more active compared to the amine analogues |
| Chitosan | Bacteria, yeast, fungi | Widely-used antimicrobial agent either alone or blended with other compounds |
| Ammonium ethyl methacrylate homopolymers | Methicillin-resistant *Staphylococcus aureus*, *Escherichia coli* | Very little or no hemolytic activity and higher inhibitory effects against Gram-positive bacteria than Gram-negative bacteria |
| Metallo-terpyridine carboxymethyl cellulose | *Staphylococcus aureus*, *Streptococcus thermophilus*, *Escherichia coli*, *Saccharomyces cerevisiae* | Minimum inhibitory concentration ranged from 6 to 8 mg/L to achieve ≥90% inhibition |
| Poly(n-vinylimidazole) modified silicone rubber | *Pseudomonas aeruginosa*, *Staphylococcus aureus* | More antibacterial activity against *Pseudomonas aeruginosa* than *Staphylococcus aureus* |

In one embodiment, the polymeric support is a biocidal biopolymer, such as chitosan or carboxymethylchitosan. In some embodiments, the enzyme is immobilized on particles, e.g., chitosan particles, such as beads, e.g., chitosan beads (e.g., microbeads), or nanoparticles. For example, the beads (e.g., microbeads) may be biodegradable. In some embodiments, the enzyme may be immobilized by encapsulation with free monomers (e.g., chitosan or carboxymethylchitosan monomers), for example, utilizing a linker.

Chitosan is a linear aminopolysaccharide of glucosamine and N-acetylglucosamine units and is obtained by alkaline deacetylation of chitin extracted from the exoskeleton of crustaceans such as shrimps and crabs, as well from the cell walls of some fungi. Chitin is a linear polymer of (1→4)-linked 2-acetamido-2-deoxy-β-D-glucopyranose (GlcNAc; A-unit), which is insoluble in aqueous solvents. It also has many structural similarities with cellulose, such as conformation of the monomers and diequatorial glycosidic linkages. Chitosan may be considered as a family of linear binary copolymers of (1→4)-linked A-units and 2-amino-2-deoxy-β-D-glucopyranose (GlcN; D-unit).

Carboxymethylchitosan (e.g., of fungal origin), e.g., N,O-carboxymethylchitosan, is >80% substituted with carboxyl groups.

Quaternary ammonium containing biopolymers, like chitosan and its more acetylated form chitin, are well known for their antimicrobial activity (Kong, et al. (2010) *Int. J. of Food Microbiol.* 144: 51-63). The antimicrobial activity of chitin, chitosan and their derivatives against different groups of microorganisms, such as bacteria, yeast, and fungi, is known.

Chitin, chitosan, and other related polymers are excellent scaffolds to immobilize enzymes (Muzzarelli (1980) *Enzyme Microb. Technol.* 2:177-184). Tyrosinase has been immobilized on chitosan for dephenolization of industrial waste (Dinçer, et al. (2012) *Int. J. Biol. Macromol.* 50:815-820) and for optical detection of phenol compounds (Abdullah, et al. (2006) *Sensors and Actuators B: Chemical* 114: 604-609). In these examples, the tyrosinase is either directly ligated to the chitosan support without a linker or using glutaraldehyde as a linker to immobilize the enzyme on chitosan. Additionally, tyrosinase-chitosan biocatalysts have been explored for the production of L-DOPA (Carvalho, et al., *Appl. Biochem. Biotechnol.* (2000) 84-86:791-800). Microbial transglutaminase has been immobilized on chitosan using glutaraldehyde as a linker for the purpose of deamidation of food proteins (Nonaka, et al. (1996) *Biosci, Biotechnol, and Biochem.* 60:532-533), using Chitopearl 3007, a microbead form of chitosan, for the polymer support, with glutaraldehyde as a linker. Extracellular tyrosinases obtainable from *Trichoderma* spp. and methods for producing them by recombinant technology are disclosed ire U.S. Pat. No. 7,910,344.

Examples of polymeric supports are provided in, for example, Nonaka, et al. (1996) *Biosci, Biotechnol, and Biochem.* 60:532-533 and Hayashi, T et al. (1991) *J Appl Polymer Sci* 42: 85-92, which is incorporated by reference herein in its entirety.

C. Linkers

In some embodiments, an enzyme as disclosed herein is immobilized on a polymer, e.g., a biocidal polymer, such as a biocidal biopolymer, e.g., chitosan, via a chemical linker, which covalently links the enzyme to the polymer. In some embodiments, the linker is an alkylene (e.g. methylene), a diimine (1,5-diimine), a diamine (1,5-diamine), dicarbonyl (e.g. 1,4-dicarbonyl), an amide bond, a polypeptide, an alkyl linker, or contains a phenyl group, a fused heterocycle, or an aromatic group, such as:

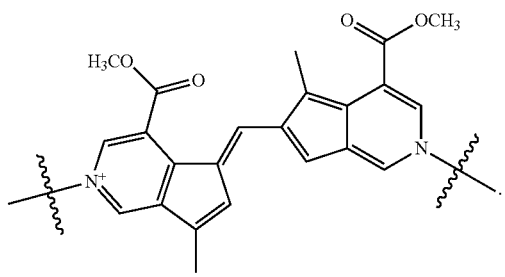 [SMILES: *n1cc2cc(/C=C3\C=C(C)c4c[n+](*)cc(C(=O)OC)c43)c(C)c-2c(C(=O)OC)c1]

Examples of reagents which can be used to provide linkers include, but are not limited to: formaldehyde, glutaraldehyde, succinate anhydride, phenolic compounds, genipin, carbodiimide reagents, proteins or peptides (e.g., zein, gelatin, collagen).

In some embodiments the linking reagent is genepin, epichlorohydrin, formaldehyde, or glutaraldehyde. (see FIG. 1). In a preferred embodiment, the linking reagent is glutaraldehyde.

In one embodiment, the enzyme is covalently linked to a carrier (polymeric support), without the use of a linker.

III. Products

Products disclosed herein include personal care products, household products, industrial food, pharmaceutical, cosmetic, healthcare, marine, painting, coating, or energy products, which include an effective amount, for example, about 0.0001% w/v to about 5% w/v, of the disclosed enzymes (e.g., zymogen-class enzyme, such as a crosslinking or lytic enzyme or other enzyme disclosed herein, e.g., a biocidal enzyme) or compositions (e.g., zymogen-class enzyme, such as a crosslinking or lytic enzyme or other enzyme disclosed herein, e.g., a biocidal enzyme, immobilized on or encapsulated in a polymer, such as a biopolymer and/or a biocidal polymer) to act as an antimicrobial agent, e.g., preservative, in the product.

In some embodiments, an enzyme or enzyme/polymer composition as disclosed herein is included as an antimicrobial agent in any of the products disclosed herein at a concentration of any of at least about 0.0001% w/v, 0.0005% w/v, 0.001% w/v, 0.005% w/v, 0.01% w/v, 0.05% w/v, 0.1% w/v, 0.5% w/v, 1% w/v, 1.5% w/v, 2% w/v, 2.5% w/v, 3% w/v, 3.5% w/v, 4% w/v, 4.5% w/v, or 5% w/v. In some embodiments, the enzyme or enzyme/polymer composition is included at a concentration of any of about 0.0001% w/v to about 0.0005% w/v, about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 1.5% w/v, about 1.5% w/v to about 2% w/v, about 2% w/v to about 2.5% w/v, about 2.5% w/v to about 3% w/v, about 3% w/v to about 3.5% w/v, about 3.5% w/v to about 4% w/v, about 4% w/v to about 4.5% w/v, about 4.5% w/v to about 5% w/v, about 0.0001% w/v to about 0.001% w/v, about 0.001% w/v to about 0.01% w/v, about 0.01% w/v to about 0.1% w/v, about 0.1% w/v to about 1% w/v, about 1% w/v to about 2.5% w/v, about 2.5% w/v to about 5% w/v, or about 1% w/v to about 5% w/v.

In some embodiments, products in which an enzyme or enzyme/polymer composition described herein is included as an antimicrobial agent do not include a petrochemically derived preservative substance, such as, but not limited to, parabens, formaldehyde and formaldehyde releasers, isothiazolinones, phenoxyethanol, and/or organic acids (such as sodium benzoate). In some embodiments, a biocidal enzyme, e.g., cross-linking or lytic enzyme, alone or in combination with a biocidal polymer, e.g., chitosan, is the only antimicrobial, e.g., antibacterial or preservative, agent in the product. In some embodiments, an enzyme as described herein (e.g., zymogen-class enzyme, such as a crosslinking or lytic enzyme or other enzyme disclosed herein, e.g., a biocidal enzyme) is included as an antimicrobial agent in combination with one or more additional antimicrobial agent(s), such as, but not limited to, one or more petrochemically derived preservative substance(s). In some embodiments, a composition as described herein (e.g., zymogen-class enzyme, such as a crosslinking or lytic enzyme or other enzyme disclosed herein, e.g., a biocidal enzyme, immobilized on or encapsulated in a polymer, such as a biopolymer and/or a biocidal polymer, for example, but not limited to, chitosan) is included as an antimicrobial agent in combination with one or more additional antimicrobial agent(s), such as, but not limited to, one or more petrochemically derived preservative substance(s).

Products disclosed herein also include industrial biocatalysis products, which include an amount of the disclosed compositions effective to remove or inactivate a biocatalyst, or biocatalytic activity, from a reaction mixture such as an industrial process (e.g., act as a purification handle for removing enzymes from industrial chemical reactions). To reduce the time and cost of biomanufacturing, "smart" biocatalytic enzyme-immobilization technologies are of interest to industries that employ biocatalysts for chemical or biologic manufacture. The enzyme immobilization platform features reversible solubility that allows for the catalyst to be employed for homogeneous catalysis at low pH conditions or heterogeneous catalysis (continuous flow) at neutral or high pH conditions. This allows for more versatility than the traditional solid support and immobilization technologies currently used. These types of stimuli responsive immobilized enzymes have been termed "smart biocatalysts"; however, their uses in industry have been limited due to a lack of commercial availability. The enzyme immobilization platform described herein will reduce the cost and time associated with purifying protein products and facilitate catalyst recycling.

The compositions described herein provide the ability to immobilize enzymes on a reversibly soluble polymer, such as a reversibly soluble biopolymer, e.g., chitosan, to streamline production to purification protocols in biomanufacturing. Chitosan demonstrates reversible solubility in water upon pH shift (soluble below pH 6.5 and insoluble above pH 6.5). Immobilized enzymes are typically employed under heterogeneous conditions (with the enzyme remaining in the solid phase, insoluble under the reaction conditions) because most carriers are insoluble organic resins derived from petrochemicals. These reactions are plagued by poor mass transfer and result in slower reaction rates and reduced product yields. Described herein is an immobilization platform that can be utilized under homogeneous conditions (in which the enzyme may exist in the liquid phase, soluble under the reaction conditions) and quickly precipitated to remove and recycle the biocatalyst. Specifically, the enzyme is "tagged" with a polymer to control solubility upon a mild shift in pH. This allows for rapid quenching of the reaction without employing excess heat or anti-solvent for removal of the enzyme, which compromises the integrity of the desired reaction product (e.g., protein product) and increases waste volume, resulting in higher manufacturing expenses.

A. Personal Care Products

An enzyme or composition, e.g., preservative composition, as described herein can be incorporated into any personal care product. Personal care products into which the disclosed compositions may be incorporated include, but are not limited to, bar soap, liquid soap (e.g., hand soap), hand sanitizer (including rinse off and leave-on alcohol based and aqueous-based hand disinfectants), preoperative skin disinfectant, cleansing wipes, disinfecting wipes, body wash, acne treatment products, antifungal diaper rash cream, antifungal skin cream, shampoo, conditioner, cosmetics (including but not limited to liquid or powder foundation, liquid or solid eyeliner, mascara, cream eye shadow, tinted powder, "pancake" type powder to be used dry or moistened, make up removal products, etc.), deodorant, antimicrobial creams, body lotion, hand cream, topical cream, aftershave lotion, skin toner, mouth wash, toothpaste, sunscreen lotion, and baby products such as, but not limited to, cleansing wipes, baby shampoo, baby soap, and diaper cream. The present subject matter may also be applied to wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc. Additional personal care products include, but are not limited to, oral products such as mouth rinse, toothpaste, dental floss coatings, veterinary and pet care products, preservative compositions, and surface disinfectants, including solutions, sprays or wipes.

The personal care product formulation typically includes a base formulation to which the preservative composition of the present disclosure is added. The base formulation may contain numerous and different ingredients depending upon the end use application. The personal care product formulation, for instance, may contain solvents, surfactants, emulsifiers, consistency factors, conditioners, emollients, skin care ingredients, moisturizers, thickeners, lubricants, fillers, antioxidants, other preservatives, active ingredients, in particular dermatologically active ingredients, fragrances and the like, as well as mixtures thereof. Active ingredients as mentioned herein include, for example, anti-inflammatories, and optionally, anti-bacterials, antifungals and the like agents. Active ingredients suited for topical applications are particularly preferred.

In some embodiments, the personal care product does not contain any additional preservatives, such as a petrochemical derived preservative substance. In some embodiments, the personal care product includes one or more additional preservative substance, such as a petrochemical derived preservative, in addition to the enzyme or enzyme/polymer composition described herein.

In some embodiments, the personal care product does not include conventional anti-bacterial and/or antifungal "active agents" that are typically included in personal care products. Conventional anti-bacterials used in hand soap include: Cloflucarban, Fluorosalan, Hexachlorophene, Hexylresorcinol, Iodine complex (ammonium ether sulfate and polyoxyethylene sorbitan monolaurate), Iodine complex (phosphate ester of alkylaryloxy polyethylene glycol), Nonylphenoxypoly (ethyleneoxy) ethanoliodine, Poloxamer-iodine complex, Povidone, Undecoylium chloride iodine complex, Methylbenzethonium chloride, Phenol, Phenol 16, Secondary amyltricresols, Sodium oxychlorosene, Tribromsalan, Triclocarban, Triclosan, and Triple dye. Conventional antimicrobials used as preservatives in consumer product formulations include: parabens, formaldehyde and formaldehyde releasers, isothiazolinones, phenoxyethanol, and organic acids (such as sodium benzoate).

In some embodiments, a biocidal enzyme, e.g., zymogen-class enzyme, such as a cross-linking or lytic enzyme, alone or in combination with (e.g., immobilized on or encapsulated in) a polymer, e.g., a biocidal polymer, such as but not limited to, chitosan, is the only antibacterial, antifungal, antimicrobial, or preservative agent in the product. In some embodiments, a biocidal enzyme, e.g., zymogen-class enzyme, such as a cross-linking or lytic enzyme, alone or in combination with (e.g., immobilized on or encapsulated in) a polymer, e.g., a biocidal polymer, such as but not limited to, chitosan, is combined with one or more additional preservative substance, such as one or more petrochemically derived preservative substance. In some embodiments, one or more biobased preservative (i.e., enzyme or enzyme/polymer composition as disclosed herein) is combined with one or more synthetic preservative (e.g., petrochemical derived substance) and the preservative (e.g., antimicrobial) effect achieved between the biobased and synthetic preservatives is additive or synergistic. In some embodiments, one or more biobased preservative (i.e., enzyme or enzyme/polymer composition as disclosed herein) is combined with one or more additional preservative substance, for example, a biocidal substance selected from polylysine, chitosan, benzoate, nisin, lysozyme, and chitosan, or any combination thereof, and the preservative (e.g., antimicrobial) effect achieved between the biobased preservative and the additional preservative substance(s) is additive or synergistic.

In some embodiments, the personal care product may include emollients. Emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

Suitable antioxidants include, e.g., sulfites (e.g., sodium sulfite), tocopherol or derivates thereof, ascorbic acid or derivates thereof, citric acid, propyl gallate, chitosan glycolate, cysteine, N-acetyl cysteine plus zinc sulfate, thiosulfates (e.g. sodium thiosulfate), polyphenols glutathione, dithiothreitol (DTT), superoxide dismutase, catalase and the like.

Chelators, such as ethylene diamine tetraacetic acid (EDTA), may also be included.

Suitable thickeners include, e.g., acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, and hydrogenated butylenes/ethylene/styrene copolymer.

Suitable moisturizers include, e.g., butylene glycol, cetyl alcohol, dimethicone, dimyristyl tartrate, glucose glycereth-26, glycerin, glyceryl stearate, hydrolyzed milk protein, lactic acid, lactose and other sugars, laureth-8, lecithin, octoxyglycerin, PEG-12, PEG 135, PEG-150, PEG-20, PEG-8, pentylene glycol, hexylene glycol, phytantriol, poly quaternium-39 PPG-20 methyl glucose ether, propylene glycol, sodium hyaluronate, sodium lactate, sodium PCA, sorbitol, succinoglycan, synthetic beeswax, tri-C14-15 alkyl citrate, and starch.

B. Household/Industrial Products

Non-limiting embodiments of household/industrial products which may incorporate the disclosed enzymes or enzyme/polymer compositions as a preservative substance, either alone or in combination with one or more additional preservative substance, such as one or more petrochemically derived preservative substance, include, but are not limited to, householder cleaners, such as concentrated liquid cleaners and spray cleaners, cleaning wipes, dish washing liquid, dish washer detergent, spray-mop liquid, furniture polish, indoor paint, outdoor paint, dusting spray, laundry detergent, fabric softener, rug/fabric cleaner, window and glass cleaner, toilet bowl cleaner, liquid/cream cleanser, etc. In a particular embodiment, the compositions described herein may be used in a food wash product, e.g., designed to clean fruits and vegetables prior to consumption. "Household products" are products, other than personal care products, that would be used by individual consumers. "Industrial products" refers to products that are used in industry.

In some embodiments, a biocidal enzyme, e.g., zymogen-class enzyme, such as a cross-linking or lytic enzyme, alone or in combination with (e.g., immobilized on or encapsulated in) a polymer, e.g., a biocidal polymer, such as but not limited to, chitosan, is combined with one or more additional preservative substance, such as one or more petrochemical derived preservative substance. In some embodiments, one or more biobased preservative (i.e., enzyme or enzyme/polymer composition as disclosed herein) is combined with one or more synthetic preservative (e.g., petrochemical derived substance) and the preservative (e.g., antimicrobial) effect achieved between the biobased and synthetic preservatives is additive or synergistic. In some embodiments, one or more biobased preservative (i.e., enzyme or enzyme/polymer composition as disclosed herein) is combined with one or more additional preservative substance, for example, a biocidal substance selected from polylysine, chitosan, benzoate, nisin, lysozyme, and chitosan, or any combination thereof, and the preservative (e.g., antimicrobial) effect achieved between the biobased preservative and the additional preservative substance(s) is additive or synergistic.

C. Other Products

Other products into which the disclosed enzymes or enzyme-polymer compositions as disclosed herein may be incorporated include, but are not limited to, food, pharmaceutical, cosmetic, healthcare, marine, paint, coating, energy (e.g., fracking fluid), plastic, packaging, and agricultural products. In some embodiments, the disclosed enzymes or enzyme-polymer compositions disclosed herein may be incorporated into HVAC systems, cooling ponds, water purification systems, or may be used in an industrial application, such as, but not limited to, pulp and paper processing.

In some embodiments, a biocidal enzyme, e.g., zymogen-class enzyme, such as a cross-linking or lytic enzyme, alone or in combination with (e.g., immobilized on or encapsulated in) a polymer, e.g., a biocidal polymer, such as but not limited to, chitosan, is combined with one or more additional preservative substance, such as one or more petrochemically derived preservative substance. In some embodiments, one or more biobased preservative (i.e., enzyme or enzyme/polymer composition as disclosed herein) is combined with one or more synthetic preservative (e.g., petrochemically derived substance) and the preservative (e.g., antimicrobial) effect achieved between the biobased and synthetic preservatives is additive or synergistic.

IV. Methods of Use

The disclosed enzymes and enzyme/polymer compositions may be used as alternatives or in addition to conventional preservatives, such as, but not limited to, parabens, formaldehyde, and glutaraldehyde and conventional biocidal agents, such as those disclosed herein, including silver (used in wound care products), in various applications that require preservatives for example, personal care, household, industrial, food, pharmaceutical, cosmetic, healthcare, marine, paint, coating, energy, plastic, packaging, and agricultural products, or in any of the products or systems disclosed herein. The disclosed enzymes and compositions are used as anti-microbial (e.g., preservative) ingredients that inhibit the growth of potentially harmful bacteria, fungi, and/or other microbes, and accordingly, are added to the product to be preserved in an effective amount to inhibit bacterial, fungal, and/or microbial growth in these products. In some embodiments, USP <51> passing criteria are achieved, i.e., for Category 2 Products: Bacteria: No less than 2.0 log reduction from the initial calculated count at 14 days, and no increase from the 14 days' count at 28 days; for Yeast and Molds: No increase from the initial calculated count at 14 and 28 days. In some embodiments, the antimicrobial behavior of the enzymes and enzyme-biopolymer coformulations are characterized by MIC (minimum inhibitory concentration) against gram-positive and gram-negative bacteria as well as fungi, which results in reduction of microbial growth by approximately 80-100%, or any of at least about 80%, 85%, 90%, 95%, 98%, or 99% of microbial growth.

When combined with a product as described herein, e.g., a personal care, household, industrial, food, pharmaceutical, cosmetic, healthcare, marine, paint, coating, energy, plastic, packaging, or agricultural product, or in any of the products or systems disclosed herein, e.g., in a formulation or incorporated into a product or system as a preservative, the composition may have effective broad spectrum preservation activity over a broad pH range.

In some embodiments, the method includes adding a preservative composition as described herein (e.g., a zymogen-class enzyme, such as a crosslinking or lytic enzyme or other enzyme disclosed herein, e.g., a biocidal enzyme) or compositions (e.g., zymogen-class enzyme, such as a cross-linking or lytic enzyme or other enzyme disclosed herein, e.g., a biocidal enzyme, immobilized on or encapsulated in a polymer, such as a biopolymer and/or a biocidal polymer to a product or system, such as a personal care, household, industrial, food, pharmaceutical, cosmetic, healthcare, marine, paint, coating, energy, plastic, packaging, or agricultural product, or in any of the products or systems disclosed herein, e.g., in a formulation or incorporated into a product or system, wherein microbial growth is decreased and/or shelf life of the product is increased in comparison to an identical product that does not contain the preservative composition. In some embodiments, the enzyme is a zymogen-class enzymes, such as an enzyme selected from a hydrolase, a protease, a lytic enzyme, a cross-linking enzyme, and combinations thereof. In some embodiments, the enzyme is a cross-linking enzyme, such as a transglutaminase, laccase, peroxidase, transferase, lysyl oxidase, or tyrosinase, or a combination thereof. In some embodiments, polymeric support is a biocidal polymer, such as chitosan or carboxymethylchitosan. In some embodiments, the enzyme is immobilized on the support via a linker. In some embodiments, no other preservative is included in the product composition, such as, but not limited to formaldehyde and/or glutaraldehyde.

In some embodiments, a method for increasing the shelf-like, integrity, or microbial free (e.g., bacterial and/or fungal free) status of a product composition, such as a personal care, household or industrial product is provided, wherein the method includes incorporating an effective amount of a preservative composition as described herein (e.g., a biocidal enzyme immobilized on a polymeric support (e.g., a biocidal polymer)) into the product (e.g., personal care, household or industrial product). In some embodiments, the effective amount may be an amount, referred to as the MIC (minimum inhibitory concentration), which results in reduction of microbial growth by approximately 80-100%, or any of at least about 80%, 85%, 90%, 95%, 98%, or 99% reduction of microbial growth as described herein.

In some embodiments of the methods or compositions described herein, an enzyme (e.g., a zymogen-class enzyme, such as a crosslinking or lytic enzyme or other enzyme disclosed herein, e.g., a biocidal enzyme) may be included at a concentration of about 0.01% w/v to about 5% w/v, or any of at least about 0.01% w/v, 0.05% w/v, 0.1% w/v, 0.5% w/v, 1% w/v, 1.5% w/v, 2% w/v, 2.5% w/v, 3% w/v, 3.5% w/v, 4% w/v, 4.5% w/v, or 5% w/v, or any of about 0.01% w/v to about 0.05% w/v, about 0.1% w/v to about 0.5% w/v, about 1% w/v to about 1.5% w/v, about 1.5% w/v to about 2% w/v, about 2% w/v to about 2.5% w/v, about 2.5% w/v to about 3% w/v, about 3% w/v to about 3.5% w/v, about 3.5% w/v to about 4% w/v, about 4% w/v to about 4.5% w/v, about 4.5% w/v to about 5% w/v, about 0.01% w/v to about 0.1% w/v, about 0.1% w/v to about 1% w/v, about 1% to about 5% w/v, about 0.05% w/v to about 0.5% w/v, about 0.5% w/v to about 5% w/v, about 1% w/v to about 2.5% w/v, or about 2.5% w/v to about 5% w/v.

In one embodiment of the methods or compositions described herein, an enzyme/polymer composition, such as a zymogen-class enzyme, such as a crosslinking or lytic enzyme or other enzyme disclosed herein, e.g., a biocidal enzyme, immobilized on or encapsulated in a polymer, such as a biopolymer and/or a biocidal polymer, may be included at a concentration of about 0.04% w/v enzyme and about 0.025% w/v polymer (such as, but not limited to, chitosan).

Examples of personal care products which may utilize the disclosed compositions of the include bar soap, liquid soap (e.g., hand soap), hand sanitizer (including rinse off and leave-on alcohol based and aqueous-based hand disinfectants), preoperative skin disinfectant, cleansing wipes, disinfecting wipes, body wash, acne treatment products, antifungal diaper rash cream, antifungal skin cream, shampoo, conditioner, cosmetics (including but not limited to liquid or powder foundation, liquid or solid eyeliner, mascara, cream eye shadow, tinted powder, "pancake" type powder to be used dry or moistened, make up removal products etc.) deodorant, antimicrobial creams, body lotion, hand cream, topical cream, aftershave lotion, skin toner, mouth wash, toothpaste, sunscreen lotion, and baby products such as, but not limited to, cleansing wipes, baby shampoo, baby soap, and diaper cream. The present subject matter may also be applied to wound care items, such as, but not limited to, wound healing ointments, creams, and lotions, wound coverings, burn wound cream, bandages, tape, and steri-strips, and medical articles such as medical gowns, caps, face masks, and shoe-covers, surgical drops, etc. Additional products include but are not limited to oral products such as mouth rinse, toothpaste, and dental floss coatings, veterinary and pet care products, preservative compositions, and surface disinfectants including solutions, sprays or wipes.

Non-limiting examples of household/industrial products which may incorporate the disclosed compositions include householder cleaners such as concentrated liquid cleaners and spray cleaners, cleaning wipes, dish washing liquid, dish washer detergent, spray-mop liquid, furniture polish, indoor paint, outdoor paint, dusting spray, laundry detergent, fabric softener, rug/fabric cleaner, window and glass cleaner, toilet bowl cleaner, liquid/cream cleanser, etc. In a particular embodiment, the compositions of the present subject matter may be used in a food wash product, designed to clean fruits and vegetables prior to consumption, packaging, and food coatings.

The following examples are intended to illustrate, but not limit, the invention.

EXAMPLES

Example 1. Transglutaminase Activity Assays

The following assays were used to assess transglutaminase enzyme activity in the compositions described in the Examples.

The residual activity of the soluble enzyme and enzyme-polymer conjugates were assayed using the standard colorimetric hydroxamate activity assay to determine specific activity or units of active enzyme (Folk and Cole, J Biol Chemistry 1965). All assays were performed at 37 C for reaction incubation times varying from 10 minutes to 2 hours.

To quantify the percent conversion and productivity of the soluble enzyme versus enzyme-polymer conjugates, HPLC based quantification was used. Briefly, the enzyme catalyzed coupling of dipeptide substrate, Cbz-Gln-Gly, and fluorescein cadaverine were surveyed at 37 C for 16 hours. The reactions were filtered to removed enzyme (or enzyme-polymer conjugates) and analyzed by HPLC to compare percent conversion.

Enzyme Preparation:

Commercially available wild-type *Streptomyces mobaraensis* transglutaminase (TI formulation) was secured from Ajinimoto. TGase is available from Ajinomoto USA under the trade name Activa-TI. This product is sold as a solid preparation of 99% maltodextrin and 1% microbial enzyme. Ajinimoto reports the enzyme activity is 81-135 U/g. The Activa-TI was used as received as well as purified from the maltodextrin by dialysis to concentrate the enzyme.

A S2P mutant form of *Streptomyces mobaraensis* transglutaminase was prepared by literature methods with a hexa-his-tag to aid in purification (Javitt, et al. (2017) *BMC Biotechnol.* 17:23). The cells were grown in shake flasks, lysed by homogenization, and the S2P-TG was isolated from the cell debris by centrifugation. The resulting semi-purified enzyme (clarified lysate) were compared on an SDS-PAGE gel, by spectroscopy, and activity for concentration of active enzyme. The S2P-TG was further purified by affinity column on a Ni-IMAC resin prior to MIC assay. The clarified lysate containing S2P-TG was compared to His-tag purified S2P-TG for polymer conjugation studies and found to perform similarly. The His-tag purified S2P-TG was used for MIC studies.

Example 2. Immobilization of Transglutaminase on Chitosan Microbeads

Chitosan microbead synthesis: A chitosan solution (1 wt % in 1% v/v acetic acid) was added dropwise to a solution of 40% v/v olive oil, 60% v/v hexadecane, and 1% v/v Tween-80, with stirring. The resulting emulsion was then crosslinked with 3% w/v glutaraldehyde. Microbeads were collected via filtration and washed with hexane, ethanol, and water.

Enzyme immobilization: The chitosan beads were pre-activated 0.1%-5% v/v glutaraldehyde at room temperature for 5 hr. Excess glutaraldehyde was removed by washing twice with water. Semi-purified enzyme (clarified lysate) was added at total protein concentration 0.2-0.4 mg/mL and incubated at 4° C. for 16 hr. Unbound enzyme was removed by washing twice with water. Negative controls containing chitosan beads and glutaraldehyde alone or chitosan beads and clarified lysate alone were also included. The samples were assayed for activity using the colorimetric hydroxamate assay and HPLC based assay.

Example 3. Stability of Transglutaminase-Bead Conjugates

Stability of transglutaminase enzyme immobilized on chitosan microbeads (prepared as described in Example 2) in pH 7.4 buffer at 4° C. over a period of 45 days was evaluated. After immobilization, the beads were washed to remove excess, unbound enzyme and resuspended in buffer, pH 7.4 and stored at 4° C. Hydroxamate assays were performed at regular intervals to assess the activity of the enzyme-bound beads by removing aliquots for assay. The samples included those beads combined with enzyme (clarified lysate) and glutaraldehyde, control beads combined with enzyme alone, and control beads treated with glutaraldehyde alone.

The results are shown in FIG. 4. Chitosan-S2P-TG microbeads maintain 92% activity at 21 days, 35% activity at 45 days, and 23% activity at 68 days when compared to the activity at day one.

Some variability in the measurements was observed, due to the heterogeneity of this sample type, and which was responsible for the apparent "increase" in activity of the sample on day 21. Because these samples were handled as a suspension of solid beads in liquid, the same volume of each sample does not necessarily contain the same number of beads. The sample volumes were too low to allow for sample preparation and processing by weight.

Example 4. Encapsulation of Transglutaminase with Free Chitosan Monomers

1% w/v free chitosan (crustacean (shrimp) chitosan (soluble at acidic pH) or fungal (mushroom) carboxymethylchitosan (soluble at neutral pH)) in 1% acetic acid was combined and incubated with transglutaminase-containing clarified lysate in 1× phosphate-buffered saline (PBS) and a linker for 16 hr at room temperature. After immobilization, the reaction was quenched and the pH of the mixture was raised through dilution into basic buffer containing primary amines (typically 50 mM Tris, pH 8.0) and 1 N NaOH added until visual precipitation was observed. The mixture was then centrifuged to collect the precipitated chitosan, effectively washing this phase of free, unbound enzyme, which remained in the supernatant. The supernatant was removed and the resulting pellet then resolubilized with pH adjustment, typically into acidic solution or buffer (either 1% acetic acid or 10 mM Tris, pH 4.3). The three samples resulting from this process, labeled "R" (Reaction), "S" (Supernatant), and "P" (Pellet), were assayed for activity using the hydroxamate assay.

The encapsulation method is shown schematically in FIG. 5.

Example 5. Stability of Carboxymethylchitosan Encapsulated Transglutaminase

Transglutaminase was immobilized by encapsulation with free carboxymethylchitosan monomers, as described in Example 4. The linker was 1-ethyl-3-(3-dimethylaminopropyl)carbodiimide hydrochloride (EDC) linker. Enzyme activity for R, S, and P samples, as described in Example 4, was determined on Day 1 and Day 75 after enzyme encapsulation, using the hydroxamate assay. Control reactions were also performed for samples prepared in the absence of enzyme, linker, and carboxymethylchitosan.

Figure 6B:
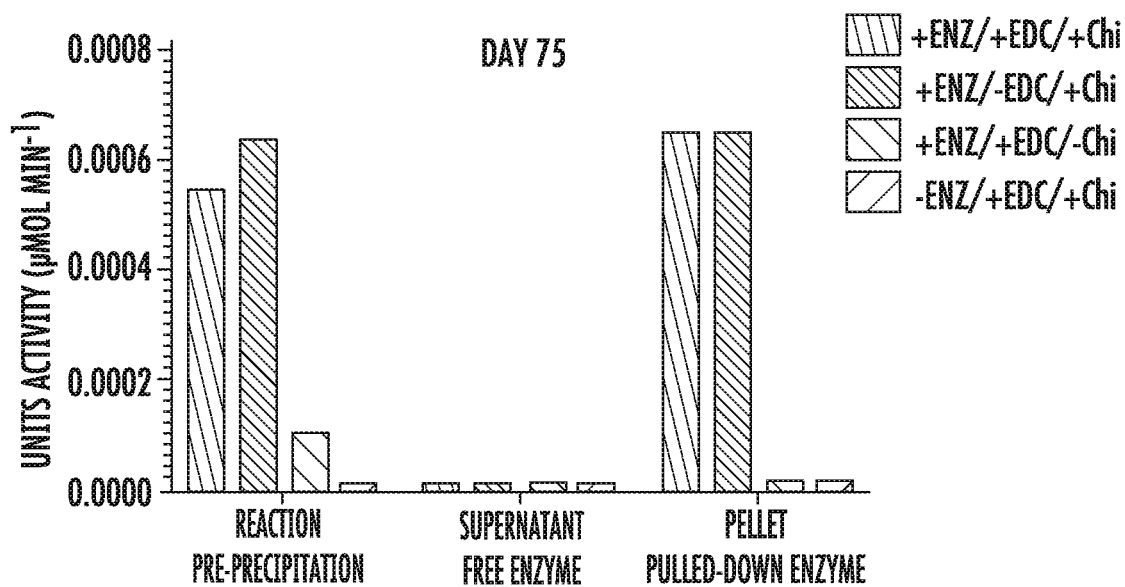

The results are shown in FIGS. 6A and 6B. Carboxymethylchitosan-S2P-TG pelleted conjugates maintain 65% activity at 75 days. The carboxymethylchitosan-S2P-TG conjugates remaining in solution (not pelleted) retain 45% activity at 75 days. S2P-TG in the absence of Carboxymethylchitosan retains less 8% of the initial activity at 75 days. S2P-TG and Carboxymethylchitosan conjugation reactions with and without EDC demonstrate similar results.

Example 6. Stability of Chitosan Encapsulated Transglutaminase

Figure 7:
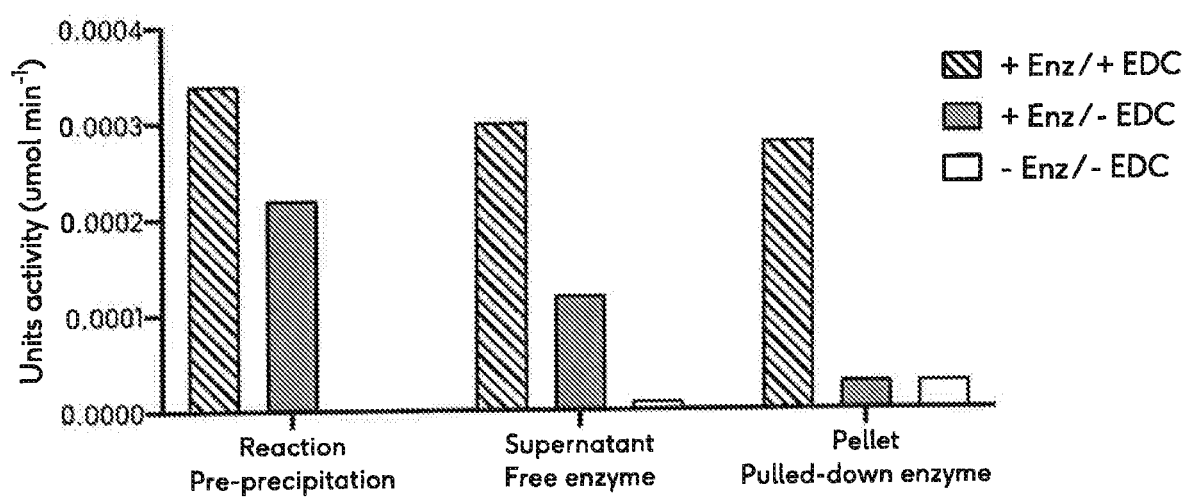
FIG. 7 shows transglutaminase activity after encapsulation with chitosan monomers as described in Example 6.

Transglutaminase was immobilized by encapsulation with free chitosan monomers, as described in Example 4. The linker was EDC. Enzyme activity on day one for R, S, and P samples, as described in Example 4, was determined. Control reactions were also performed for samples prepared in the absence of enzyme and linker. The results are shown in FIG. 7. One day one, excess unbound enzyme was removed by centrifugation and removal of the supernatant. The resolubilized pellet (P) containing EDC, S2P-TG, and chitosan together is the sole reaction that demonstrates enzymatic activity (roughly 82% of the total enzyme activity is retained). In the absence of EDC the enzyme is removed in the supernatant and the resulting pellet has less than 9% of the initial signal, which is within the background of this assay as seen by the white bar showing the signal contributed by chitosan alone without enzyme or EDC present.

Figure 8A:
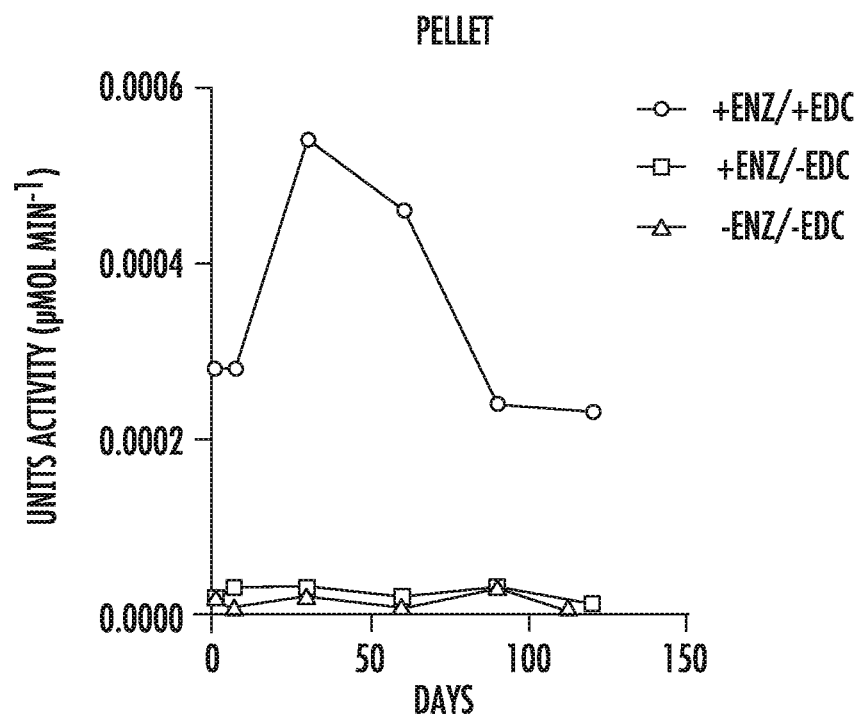
FIGS. 8A-8B show stability of chitosan encapsulated transglutaminase as described in Example 6.
Figure 8B:
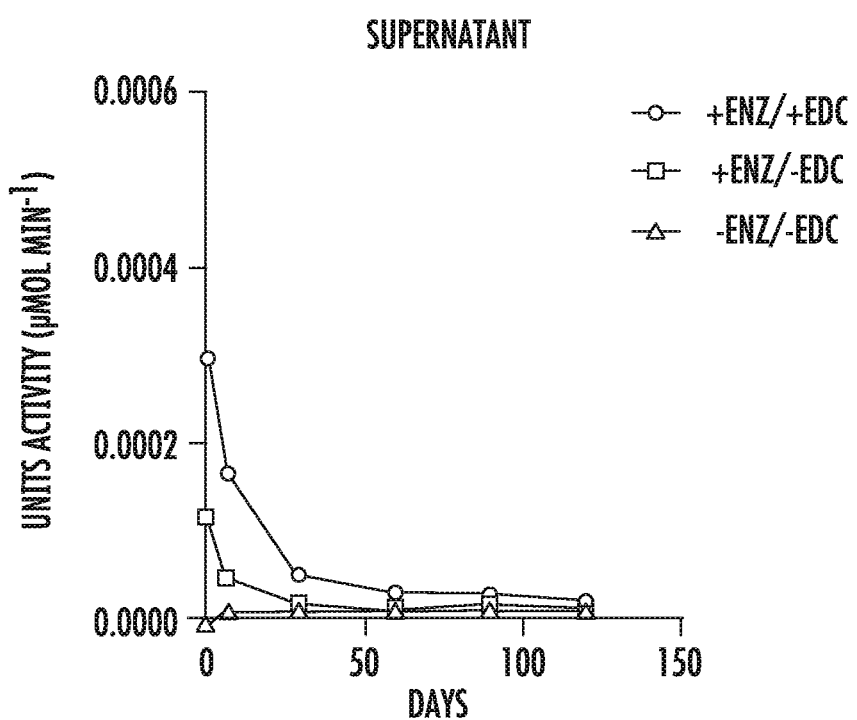
Figure 9A:
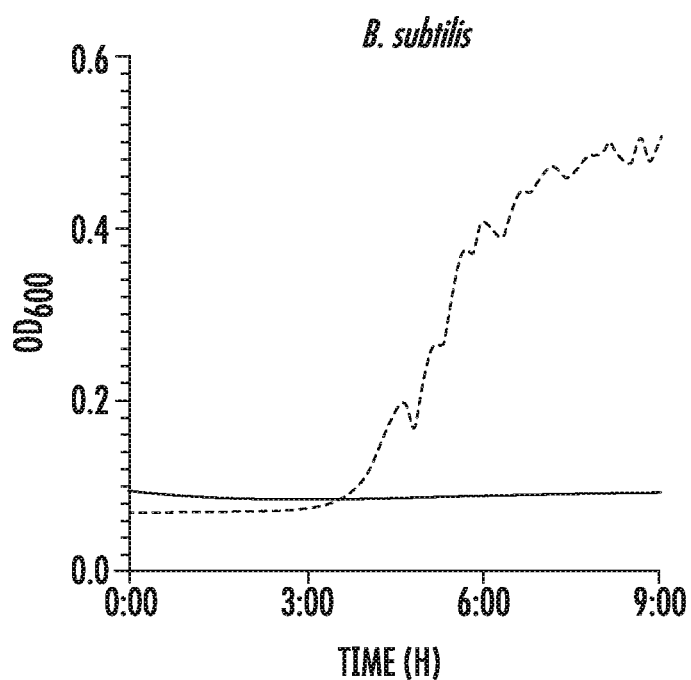
FIG. 9A shows growth inhibition of *B. subtilis* in the presence of 312 mg $L^{-1}$ (or 0.03% w/v) Curie Co mTG (solid black line). Dashed grey line shows growth in media only.
Figure 9B:
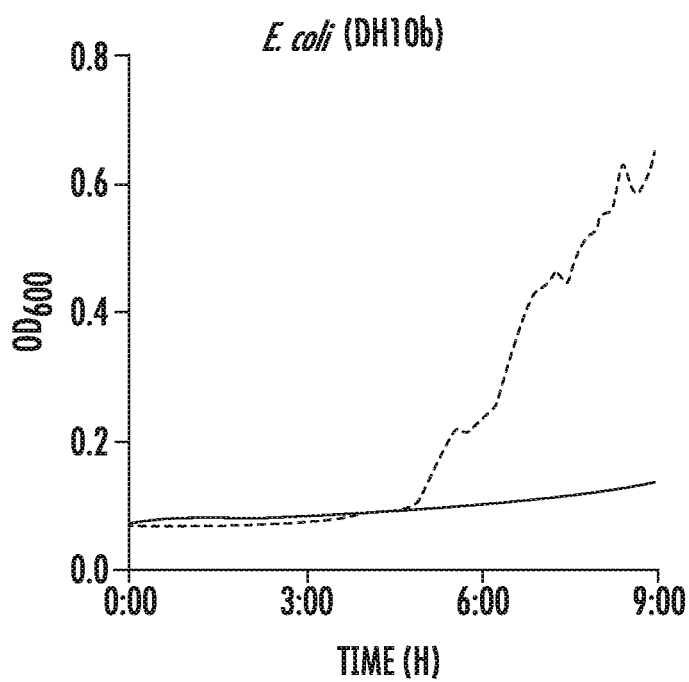
FIG. 9B shows growth inhibition of *E. coli* (DH10b, cloning strain) in the presence of 880 mg $L^{-1}$ (0.088% w/v) Curie Co mTG (solid black line). Dashed grey line shows growth in media only.

Enzyme activity of the S and P samples was tracked for 120 days using the hydroxamate assay and confirmed by HPLC based activity assay. The results are shown in FIGS. 8A and 8B. The HPLC assay was used to corroborate the activity findings after 60 days and 120 days, and were in excellent agreement with the hydroxymate assay activity retention trends. The resolubilized pellet (P) containing EDC, S2P-TG, and chitosan together is the sole experiment that demonstrated and retained enzymatic activity after precipitation. This sample retained activity over a 4 month period at pH 4.5. After the chitosan was precipitated, the supernatant (S) was isolate, which contains unbound enzyme. The supernatant (S) was also monitored over 120 days. These sample showed a rapid decline in residual enzyme activity, with roughly 15% enzyme activity remaining after 30 days.

Example 7. MIC Determination

To perform the minimum inhibitory concentration (MIC) testing, a culture with 4 mL media was inoculated by scratching from a frozen glycerol stock and grown overnight at either 30° C. for *C. albicans* or 37° C. for *E. coli* or *B. subtilis*. The overnight culture was then diluted to an $OD_{600}$ of 6.4E-03 and 2 µL of the diluted culture was inoculated into each well of a 96 well plate containing 100 µL of media and the appropriate volume of the treatment conditions tested (enzyme, chitosan, or both). The plate was then incubated with shaking at the appropriate temperature for the strain being tested in a plate reader (Biotek Synergy H1) and the optical density at 600 nm recorded every 10 min over the course of the assay (9-18 hours). To assay for cell viability at the conclusion of the experiment, the BacTiter Glo assay was performed according to the manufacturer's instructions with 25 µL of each culture and 25 µL of BacTiter Glo Assay Reagent in a black-walled 96 well half area plate (Promega). The assay was incubated with shaking for 5 minutes at room temperature and then the luminescent signal intensity quantified.

Results are shown in FIGS. 9A-9D.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific embodiments of the method and compositions described herein. Such equivalents are intended to be encompassed by the following claims.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for preserving a product comprising incorporating at least one cross-linking enzyme in an effective amount to provide antimicrobial activity in comparison to a product not comprising the cross-linking enzyme,
wherein the cross-linking enzyme is selected from microbial transglutaminase, tyrosinase, and lysyl oxidase.

2. The method of claim 1 wherein the cross-linking enzyme is immobilized on or encapsulated within a polymeric support.

3. The method of claim 2 wherein the method further comprises incorporating at least one other antimicrobial substance in addition to the cross-linking enzyme.

4. The method of claim 2 or 3 wherein the polymeric support comprises a biocidal polymer.

5. The method of claim 4 wherein the biocidal polymer is chitin, chitosan, carboxymethylchitosan, polylysine, cellulose, quaternary ammonium cellulose, alginate, pectin, carboxycellulose, or a combination thereof.

6. The method of claim 1 wherein the method further comprises incorporating at least one other antimicrobial substance in addition to the cross-linking enzyme.

* * * * *